(12) United States Patent
Voit et al.

(10) Patent No.: US 11,584,867 B2
(45) Date of Patent: *Feb. 21, 2023

(54) BIO-ELECTRONIC DEVICES INCLUDING HYDROLYTICALLY STABLE POLYMERS

(71) Applicant: Board of Regents, The University of Texas System, Austin, TX (US)

(72) Inventors: Walter Voit, Austin, TX (US); Melanie Ecker, Austin, TX (US); Seyed Mahmoud Hosseini, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/569,702

(22) Filed: Jan. 6, 2022

(65) Prior Publication Data

US 2022/0127493 A1 Apr. 28, 2022

Related U.S. Application Data

(63) Continuation of application No. 16/677,243, filed on Nov. 7, 2019, now Pat. No. 11,261,345.

(60) Provisional application No. 62/760,582, filed on Nov. 13, 2018.

(51) Int. Cl.
| | | |
|---|---|---|
| *C09D 181/02* | (2006.01) | |
| *C08G 75/045* | (2016.01) | |
| *A61N 1/05* | (2006.01) | |
| *A61B 5/24* | (2021.01) | |

(52) U.S. Cl.
CPC .............. *C09D 181/02* (2013.01); *A61B 5/24* (2021.01); *A61N 1/0551* (2013.01); *C08G 75/045* (2013.01); *A61B 2562/0209* (2013.01)

(58) Field of Classification Search
CPC ..... C08G 75/04; C08G 75/045; C09D 181/02
See application file for complete search history.

(56) References Cited

U.S. PATENT DOCUMENTS

| | | |
|---|---|---|
| 9,597,693 B1 | 3/2017 | Byers et al. |
| 9,877,898 B2 | 1/2018 | Moszner et al. |
| 2008/0090399 A1 | 4/2008 | Malik et al. |
| 2008/0119711 A1 | 5/2008 | Nikumb et al. |
| 2011/0319559 A1 | 12/2011 | Kania et al. |
| 2012/0161088 A1 | 6/2012 | Choi et al. |
| 2014/0008244 A1 | 1/2014 | Kavusi et al. |
| 2014/0323647 A1 | 10/2014 | Voit et al. |
| 2015/0250687 A1 | 9/2015 | Bowman et al. |
| 2017/0267804 A1 * | 9/2017 | Ellson .................... C08G 18/73 |

FOREIGN PATENT DOCUMENTS

| | | |
|---|---|---|
| CN | 108779225 A | 11/2018 |
| JP | 2012153794 A | 8/2012 |
| KR | 101826496 B1 | 2/2018 |
| KR | 101840335 B1 | 3/2018 |
| WO | 2009010423 A1 | 1/2009 |
| WO | 2009132070 A2 | 10/2009 |
| WO | 2014078282 A1 | 5/2014 |
| WO | 2017034858 A1 | 3/2017 |
| WO | 2017160810 A1 | 9/2017 |
| WO | WO-2017160810 A1 * | 9/2017 ......... C08G 18/1841 |
| WO | 2018005365 A1 | 1/2018 |

OTHER PUBLICATIONS

Lundberg, et a;. "Poly(ethylene glycol)-Based Thiol-ene Hydrogel Coatings-Curing Chemistry, Aqueous Stability, and Potential Marine Antifouling Applications", Applied Materials & Interfaces, 2(3), p. 903-912, 2010. (Year: 2010).*
Garcia-Sandoval, et al.; "Stable softening bioelectronics: A paradigm for chronically viable ester-free neural interfaces such as spinal cord stimulation implants"; Elsevier; Biomaterials, vol. 227; Aug. 16, 2021; 12 pgs.
Nair, et al.; "Photopolymerized thiol-ene systems as shape memory polymers"; Elsevier; Polymer, vol. 51, No. 19; Sep. 1, 2010; 7 pgs.
Leng, et al.; "Shape-Memory Polymers and Multifunctional Composites"; CRC Press; http://www.crcpress.com; Taylor & Francis Group; http://www.taylorandfrancis.com; 2010; 374 pgs.
Nguyen, et al.; "Mechanically-compliant intracortical implants reduce the neuroinflammatory response"; Journal of Neural Engineering, 11, 056014; doi:10.1088/1741-2560/056014; IOP Publishing; Aug. 15, 2014; 15 pgs.
Guzman, et al.; "Novel thermal curing of cycloaliphatic resins by thiol-epoxy click process with several multifunctional thiols"; Research Article; Polymer International, 66; Society of Chemical Industry; www.soci.org; Wiley Online Library; wileyonlinelibrary.com; DOI 10.1002/pi.5336; Jan. 20, 2017; 11 pgs.
Podgorski, et al.; "Development of Glassy Step-Growth Thiol-Vinyl Sulfone Polymer Networks"; Macromolecular Journals; Macromolecular Rapid Communications; wileyonlinelibrary.com; DOI:10.1002/marc.201400260; 2014; 6 pgs.
Reinelt, et al.; "Synthesis and Photopolymerization of Thiol-Modified Triazine-Based Monomers and Oligomers for the Use in Thiol-Ene-Based Dental Composites"; Macromolecular Jounrals; Macromolecular Chemistry and Physics; www.mcp-journal.de; wileyonlinelibrary.com; DOI:10.1002/macp.201400174; 2014; 11pgs.
Podgorski, et al.; "Programmable Mechanically Assisted Geometric Deformations of Glassy Two-Stage Reactive Polymeric Materials"; ACS Applied Materials & Interfaces; www.acsami.org; ACS Publications; American Chemical Society; dx.doi.org/10.1021/am40537r; Jan. 10, 2014; 9 pgs.
Qu, et al.; "1,n-Alkanedithiol (n=2,4,6,8,10) Self-Assembled Monolayers on Au(111): Electrochemical and Theoretical Approach"; Bull. Korean Chem. Soc.; vol. 30, No. 11; 2009; 6 pgs.
Hosseini, et al.; "Softening Shape Memory Polymer Substrates for Bioelectronic Devices With Improved Hydrolytic Stability"; Frontiers in Materials; www.frontiersin.org; vol. 5, Article 66; Nov. 15, 2018; 12 pgs.

(Continued)

*Primary Examiner* — Christopher M Rodd

(57) ABSTRACT

Bio-electronic devices including a substrate layer composed of a thiol-ene shape memory polymer, the polymer including, a sequential chain of a first type of monomer covalently bonded to a second type of monomer via thiol-ene linkages that form a backbone of the polymer, and, at least one patterned gold interconnect line adhered to the substrate layer.

3 Claims, 18 Drawing Sheets

(56) References Cited

OTHER PUBLICATIONS

Lundberg, et al.; "Poly(ethylene glycol)-Based Thiol-ene Hydrogel Coatings—Curing Chemistry, Aqueous Stability, and Potential Marine Antifouling Applications"; www.acsami.org; vol. 2, No. 3; Applied Materials & Interfaces; 2010; 10 pgs.

"Standard Guide for Accelerated Aging of Sterile Barrier Systems for Medical Devices"; ASTM International; Designation: F1980-16; Sep. 2016; 7 pgs.

Baer, et al.; "Shape-Memory Behavior of Thermally Stimulated Polyurethane for Medical Applications"; Wiley InterScience; www.interscience.wiley.com; DOI 10.102/app.25567; Journal of Applied Polymer Science, vol. 103, 3882-3892; Sep. 27, 2006; 11 pgs.

Barrett, et al.; "Qualification of Elastic Memory Composite Hinges for Spaceflight Applications"; American Institute of Aeronautics and Astronautics; May 2006; 11 pgs.

Baudis, et al.; "Smart Polymers for Biomedical Applications"; Maromolecular Journals; Macromolecular Chemistry and Physics; wileyonlinelibrary.com; www.mcp-journal.de; DOI: 10.1002/macp.201400561; 2014; 4 pgs.

Black, et al.; "In vitro compatibility testing of thiol-ene/acrylate-based shape memory polymers for use in implantable neural interfaces"; Society for Biomaterials; Wiley Peroidicals, Inc.; Wiley Online Library; wileyonlinelibrary.com; DOI: 10.1002/jbm.a.36478; May 24, 2018; 8 pgs.

Buckley, et al.; "Inductively Heated Shape Memory Polymer for the Magnetic Actuation of Medical Devices"; IEEE Transactions on Biomedical Engineering, vol. 53, No. 10; Oct. 2006; 9 pgs.

Charkhkar, et al.; "Use of cortical neuronal networks for in vitro material biocompatibility testing"; Elsevier; www.elsevier.com/locate/bios; Biosensors and Bioelectronics 53 316-323; 2014; 8 pgs.

Dietsch, et al.; A Review—Features and Benefits of Shape Memory Polymers (SMPs); Cornerstone Research Group Inc.; vol. 39, No. 2; Apr. 2007; 10 pgs.

Do, et al.; "Characterization of a Thiol-Ene/Acrylate-Based Polymer for Neuroprosthetic Implants"; ACS Omega; ACS Publications; http://pubs.acs.org/journal/acsodf; American Chemical Society; DOI: 10.1021/acsomegs.7b00834 Aug. 16, 2017; 8 pgs.

Ecker, et al.; "Sterilization of Thiol-ene/Acrylate Based Shape Memory Polymers for Biomedical Applications"; Macromolecular Journals; Macromolecular Materials and Engineering; wileyonlinelibrary.com; www.mme-journal.de; DOI: 10.1002/mame.201600331; 2017; 10 pgs.

Ecker, et al.; "Durability of switchable QR code carriers under hydrolytic and photolytic conditions"; IOP Publishing; Smart Materials and Structures; doi: 10.1088/0964-1726/22/9/094005; Aug. 27, 2013; 11 pgs.

Ecker, et al.; "Multifunctionsl poly(ester urethane) laminates with encoded information"; RSC Advances; Royal Society of Chemistry; www.rsc.org/advances; DOI: 10.1039/c3ra45651j; Nov. 6, 2013; 7 pgs.

Ecker, et al.; "Novel design approaches for multifunctional information carriers"; RSC Advances; Royal Society of Chemistry; www.rsc.org/advances; DOI: 10.1039/c4ra08977d; Sep. 17, 2017; 9 pgs.

Feninat, et al.; "Shape Memory Materials for Biomedical Applications"; Advanced Engineering Materials, 4, No. 3; 1438-1656/02/0303-009; 2002; 14 pgs.

Garcia-Sandoval, et al.; "Chronic softening spinal cord stimulation arrays"; IOP Publishing; Journal of Neural Engineering; 045002; https://doi.org/10.1088/1741-2552/aab90d; 2018; 18 pgs.

Gregori, et al.; "Selective oxidation of sulfides to sulfoxides and sulfones using 30% aqueous hydrogen peroxide and silica-vanadia catalyst"; Elsevier; Journal of Molecular Catalysis A: Chemical; www.elsevier.com/locate/molcata; Feb. 11, 2008; 4 pgs.

Hager, et al.; "Shape memory polymers: Past, present and future developments"; Elsevier; Progress in Polymer Science; www.elsevier.com/locate/ppolysci; http://dx.doi.org/10.1016/j.progpolymsci.2015.04.002; Apr. 14, 2015; 31 pgs.

Hemmerich; "General Aging Theory and Simplified Protocol for Accelerated Aging of Medical Devices" MDDI Online; https://www.mddionline.com/general-aging-theory-and-simplified-protocol-accelerated-aging-medical-devices; Jul. 1, 1998; 4 pgs.

Hu, et al.; "A review of actively moving polymers in textile applications"; Journal of Materials Chemistry; www.rsc.org/materials; DOI: 10.1039/b922872a; The Royal Society of Chemistry; 2010; 10 pgs.

Hu, et al.; "A review of stimuli-responsive polymers for smart textile applications"; IOP Publishing; Smart Materials and Structures; 053001; dio:10.1088/0964-1726/21/5/053001; stacks.iop.org/SMS/21/053001; Apr. 18, 2012; 24 pgs.

Hu, et al.; "Recent advances in shape-memory polymers: Structure, mechanism, functionality, modeling and applications"; Elsevier; Progress in Polymer Science; www.elsevier.com/locate/ppolysci; http://dx.doi.org/10.1016/j.progpolymsci.2012.06.001; Jun. 12, 2012; 44 pgs.

Huang, et al.; "An optical probe for detecting chondrocyte apoptosis in response to mechanical injury"; Scientific Reports; www.nature.com/scientificreports; DOI:10.1038/s41598-017-10653-y; Sep. 7, 2017; 10 pgs.

Immergut, et al.; "Principles of Plasticization"; Polytechnic Institute of Brooklyn; Advances in Chemistry; American Chemical Society; Jan. 1, 1965; 26 pgs.

Ishizawa, et al.; "Research on Application of Shape Memory Polymers to Space Inflatable Systems"; Proceeding of the 7th International Symposium on Artificial Intelligence, Robotics and Automation in Space: i-SAIRAS 2003, NAR, Japan; May 19-23, 2003; 4 pgs.

"Biological evaluation of medical devises—Part 5: Tests for in vitro cytotoxicity"; International Standard; Reference No. ISO 10993-5:2009(E); Third edition; Jun. 1, 2009; 42 pgs.

Jeyakumar, et al.; "Selective oxidation of sulfides to sulfoxides and sulfones at room temperature using H2O2 and Mo (VI) salt as catalyst"; Elsevier; Science Direct; Tetrahedron Letters; www.sciencedirect.com; doi:10.1016/j.tetlet.2006.04.153; May 22, 2006; 4 pgs.

Johnson, et al.; "Biocompatibility of precious metals for medical applications"; DOI:10.1533/9780857099051.1.37; Elsevier Ltd; 2014; 19 pgs.

Kulshrestha, et al.; "Polymers for Biomedical Applications"; ACS Symposium Series; American Chemical Society; 2008; 7 pgs.

Lecomte, et al.; "In vitro and in vivo biostability assessment of chronically-implanted Parylene C neural sensors"; Elsevier; Sensors and Actuators B: Chemical; ScienceDirect; www.elsevier.com/locate/snb; http://dx.doi.org/10.1016/j.snb.2017.05.057; May 23, 2017; 8 pgs.

Behl, et al.; "Shape-Memory Polymers and Shape-Changing Polymers"; Adv Polym Sci; DOI:10.1007/12_2009_26; Jan. 2010; 218 pgs.

Lenedlein, et al.; "Shape-Memory Polymers for Biomedical Applications"; Advances in Science and Technology; ISSN:1662-0356, vol. 54; doi:10.4028/www.scientific.net/AST.54.96; Sep. 2, 2008; 8 pgs.

Liu, et al.; "Review of progress in shape-memory polymers"; Journal of Materials Chemistry; www.rsc.org/materials; The Royal Society of Chemistry; DOI:10.1039/b615954k; Mar. 19, 2007; 16 pgs.

Lundberg, et al.; "Poly(ethylene glycol)-Based Thiol-ene Hydrogel Coatings-Curing Chemistry, Aqueous Stability, and Potential Marine Antifouling Applications"; ACS Applied Materials & Interfaces; vol. 2, No. 3; www.acsami.org; Feb. 18, 2010; 10 pgs.

Lyu, et al.; "Degradability of Polymers for Implantable Biomedical Devices"; International Journal of Molecular Sciences; ISSN 1422-0067; www.mdpi.com/journal/ijms; doi:10.3390/ijms10094033; Sep. 11, 2009; 33 pgs.

Mather, et al.; "Shape Memory Polymer Research"; The Annual Review of Materials Research online at matsci.annualreviews.org; doi:10.1146/annurev-matsci-082908-145419; 2009; 29 pgs.

Mattila, et al.; "Intelligent textiles and clothing"; Woodhead Publishing in Textiles; The Textile Institute; CRC Press; 2006; 525 pgs.

(56) References Cited

OTHER PUBLICATIONS

Pretsch, et al.; "Switchable information carriers based on shape memory polymer"; Journal of Materials Chemistry; www.rsc.org/materials; DOI:10.1039/c2jm16204k; The Royal Society of Chemistry; Jan. 25, 2012; 11 pgs.

Reit, et al.; "Hydrolytically Stable Thiol-ene Networks for Flexible Bioelectronics"; ACS Applied Materials & Interfaces: www.acsami.org; ACS Publications; American Chemical Society; DOI:10.1021/acsami.5b10593; Dec. 9, 2015; 9 pgs.

Rubehn, et al.; "In vitro evaluation of the long-term stability of polyimide as a material for neural implants"; Elsevier; Biomaterials; ScienceDirect; www.elsevier.com/locate/biomaterials; Feb. 9, 2010; 10 pgs.

Ryu, et al.; "Human cortical prostheses:lost in translation:"; National Institutes of Health; Neurosurg Focus; doi:10.3171/2009.4.FOCUS0987; Jul. 2009; 21 pgs.

Shoffstall, et al.; "A Mosquito Inspired Strategy to Implant Microprobes into the Brain"; Scientific Reports; www.nature.com/scientificreports; DOI:10.1038/s41598-017-18522-4; Jan. 9, 2018; 10 pgs.

Simon, et al.; "Design and demonstration of an intracortical probe technology with tunable modulus"; Society for Biomaterials; Wiley Online Library; wileyonlinelibrary.com; DOI:10.1002/jbm.a.35896; Sep. 7, 2016; 10 pgs.

Singhal, et al.; "Controlling the Actuation Rate of Low-Density Shape-Memory Polymer Foams in Water"; National Institutes of Health; Macromol Chem Phys.; doi:10.1002/macp.201200342; Jun. 13, 2013; 28 pgs.

Takmakov, et al.; "Rapid evaluation of the durability of cortical neural implants using accelerated aging with reactive oxygen species"; Department of Health & Human Services; J Neural Eng.; stacks.iop.org/JNE/12/026003/mmedia; DOI:10.1088/1741-2560/12/2/026003; Apr. 2015; 29 pgs.

Teo, et al.; "Polymeric Biomaterials for Medical Implants and Devices"; ACS Biomaterials Science & Engineering; pubs.acs.org/journal/abseba; ACS Publications; DOI:10.1021/acsbiomaterials.5b00429; 2016; 19 pgs.

Wang, et al.; "A mini review: Shape memory polymers for biomedical applications"; Department de Chimie, Universite de Montreal; Front. Chem. Sci. Eng.; DOI:10.1007/s11705-017-1632-4; Jan. 1, 2017; 11 pgs.

Ware, et al.; "Thiol-Click Chemistries for Responsive Neural Interfacesa"; Department of Health & Human Services; Macromol Biosci.; doi:10.1002/mabi.201300272; Wiley Online Library; Dec. 2013; 12 pgs.

Ware, et al.; "Thiol-ene/acrylate substrates for softening intracortical electrodes"; Society for Biomaterials; Wiley Periodicals, Inc.; Wiley Online Library; wileyonlinelibrary.com; 10.1002/jbm.b.32946; May 13, 2013; 11 pgs.

Liu, et al.; "Shape memory polymers and their composites in aerospace applications: a review"; IOP Publishing; Smart Materials and Structures; doi:10.1088/0964-1726/23/2/023001; Jan. 9, 2014; 23 pgs.

\* cited by examiner

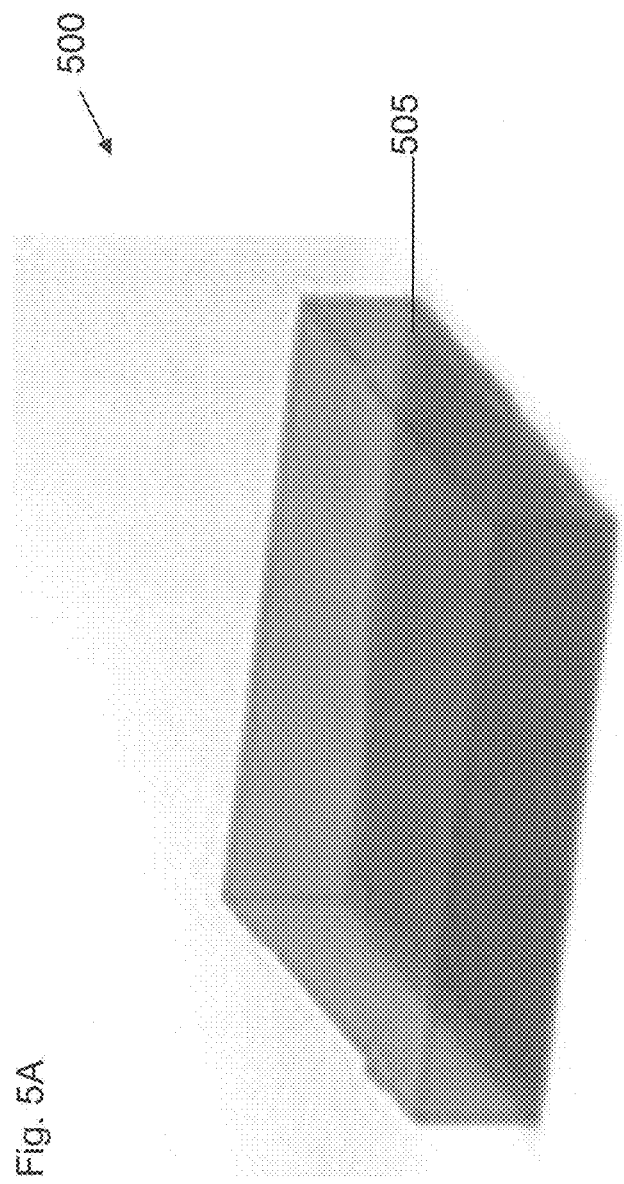

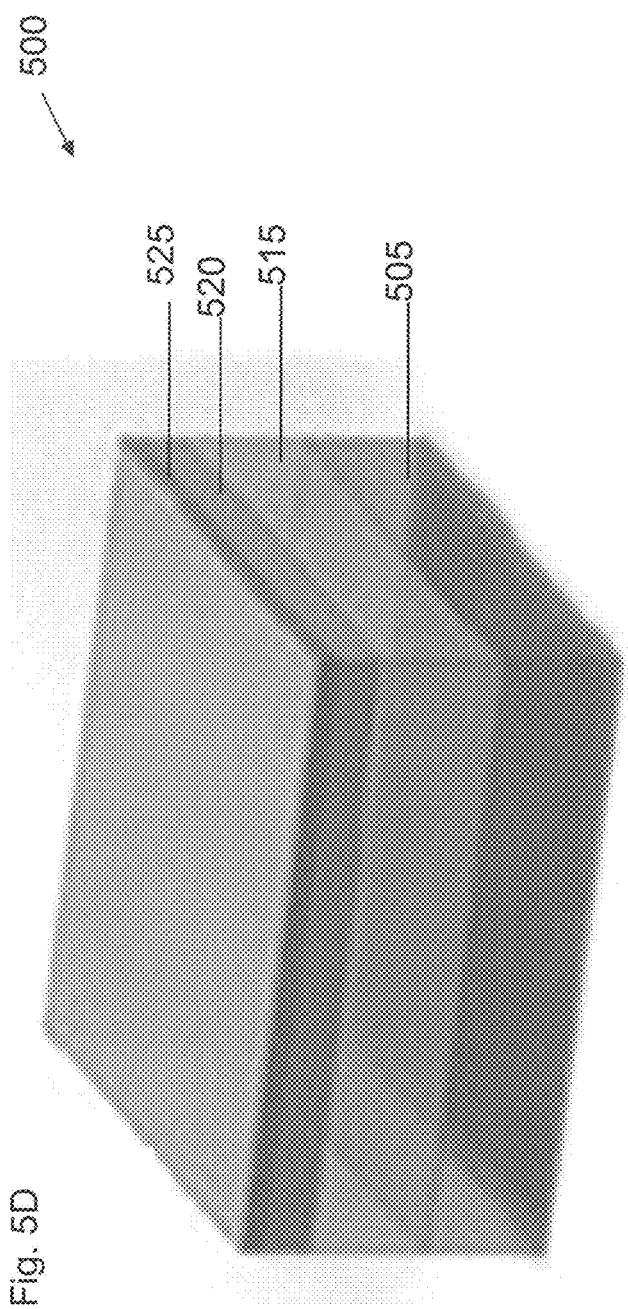

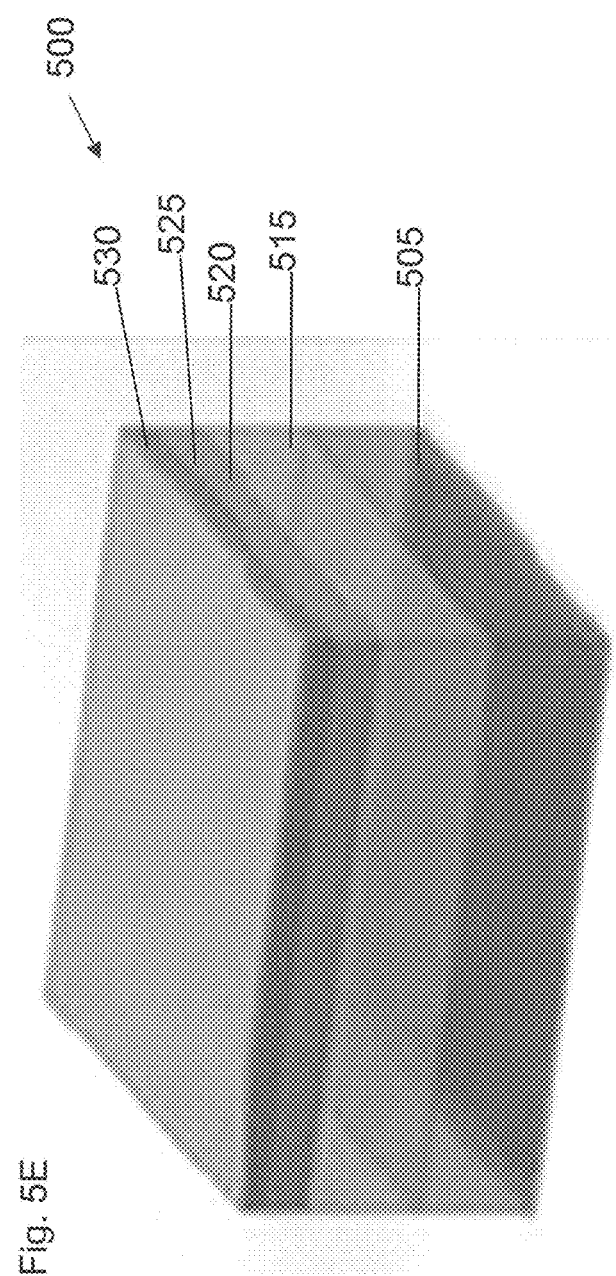

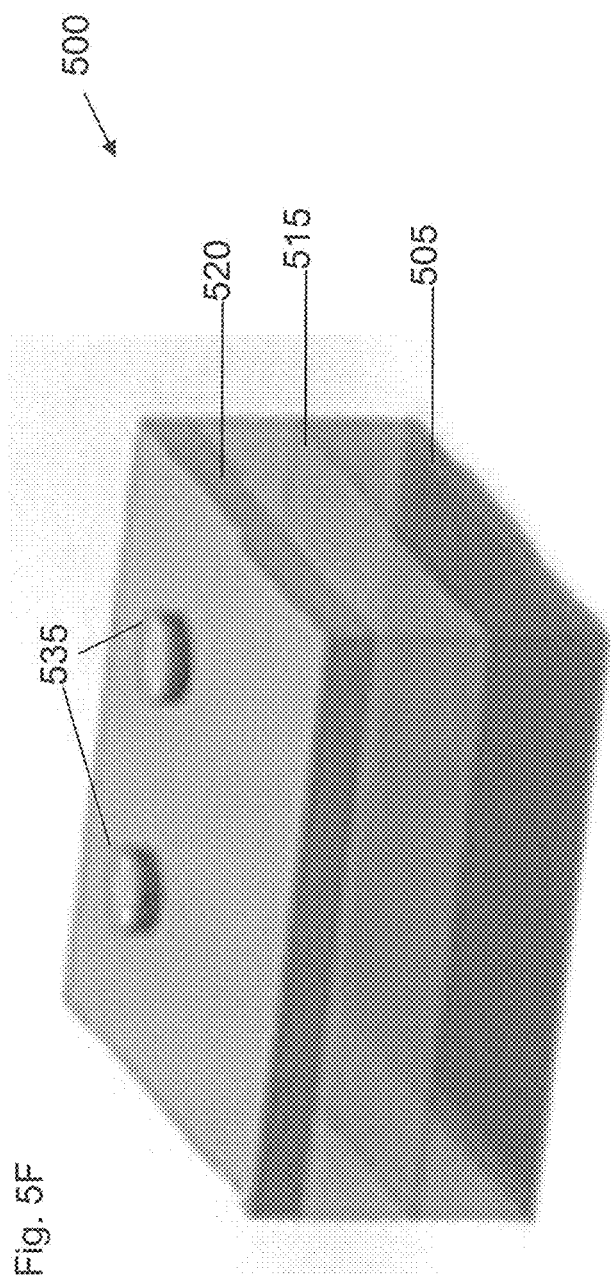

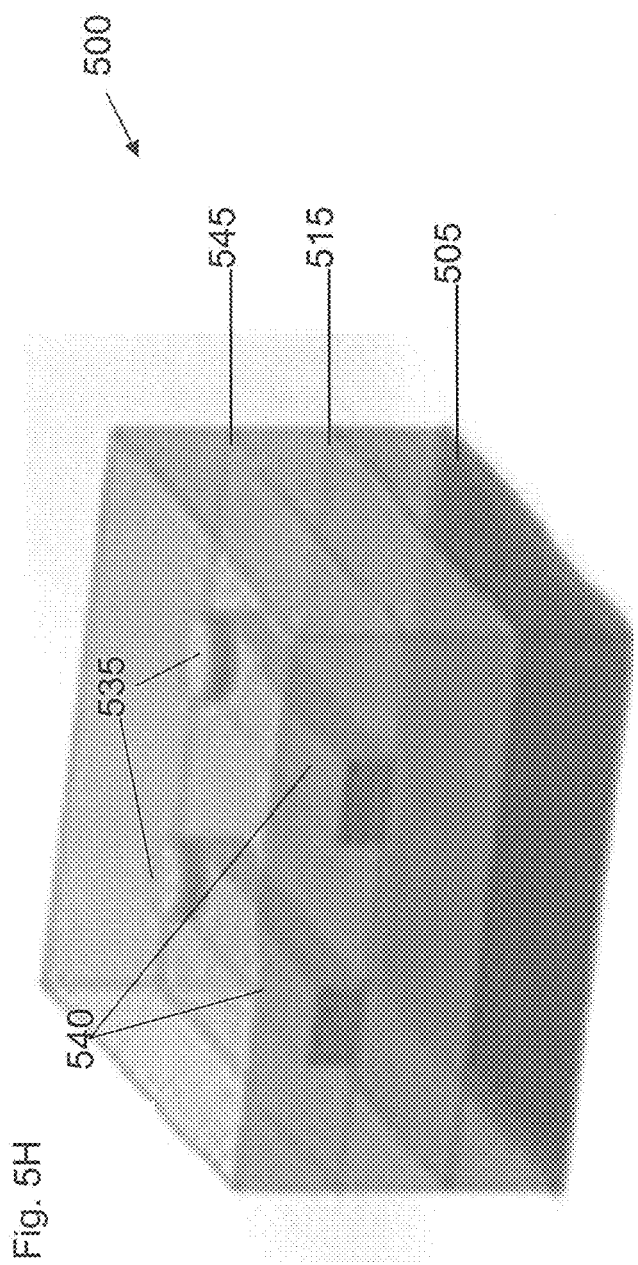

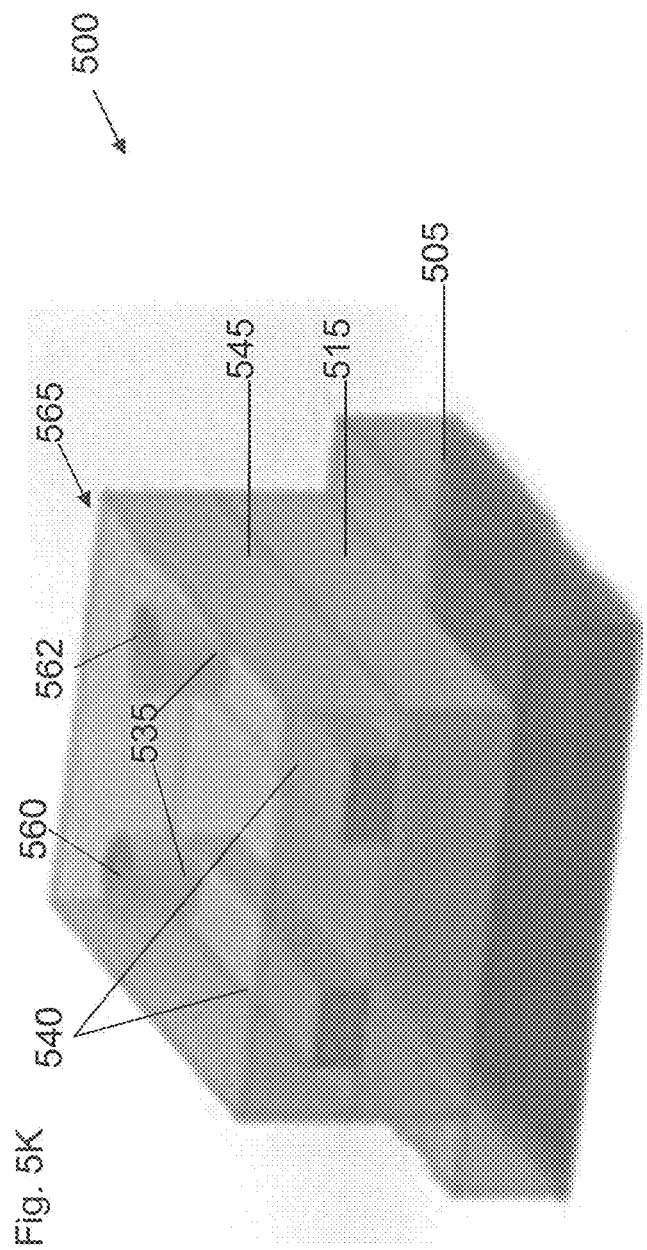

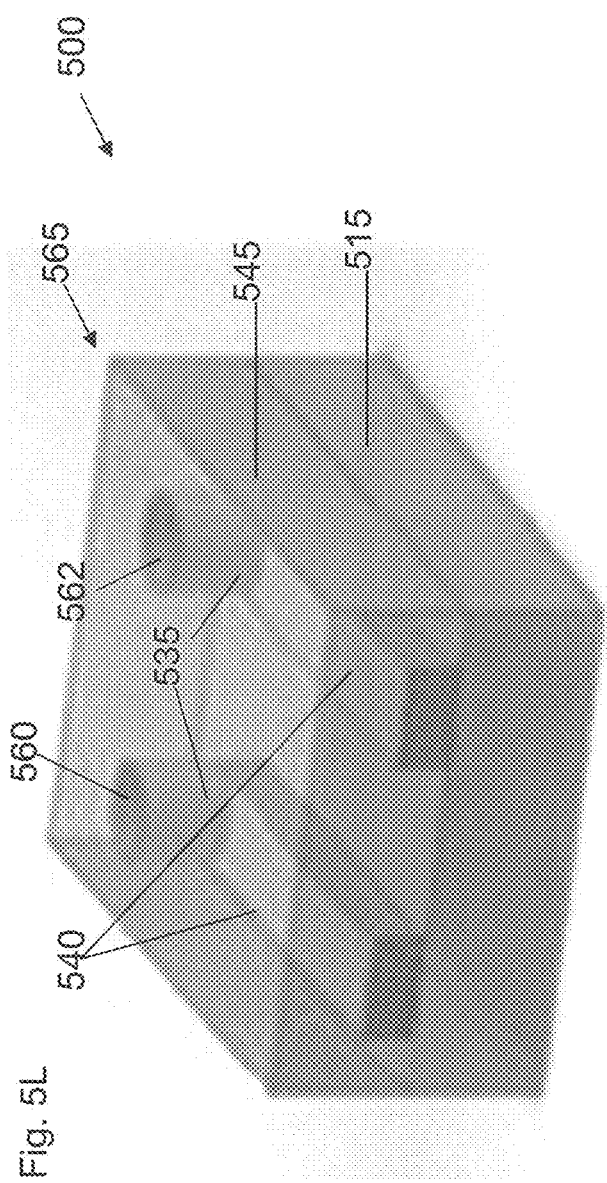

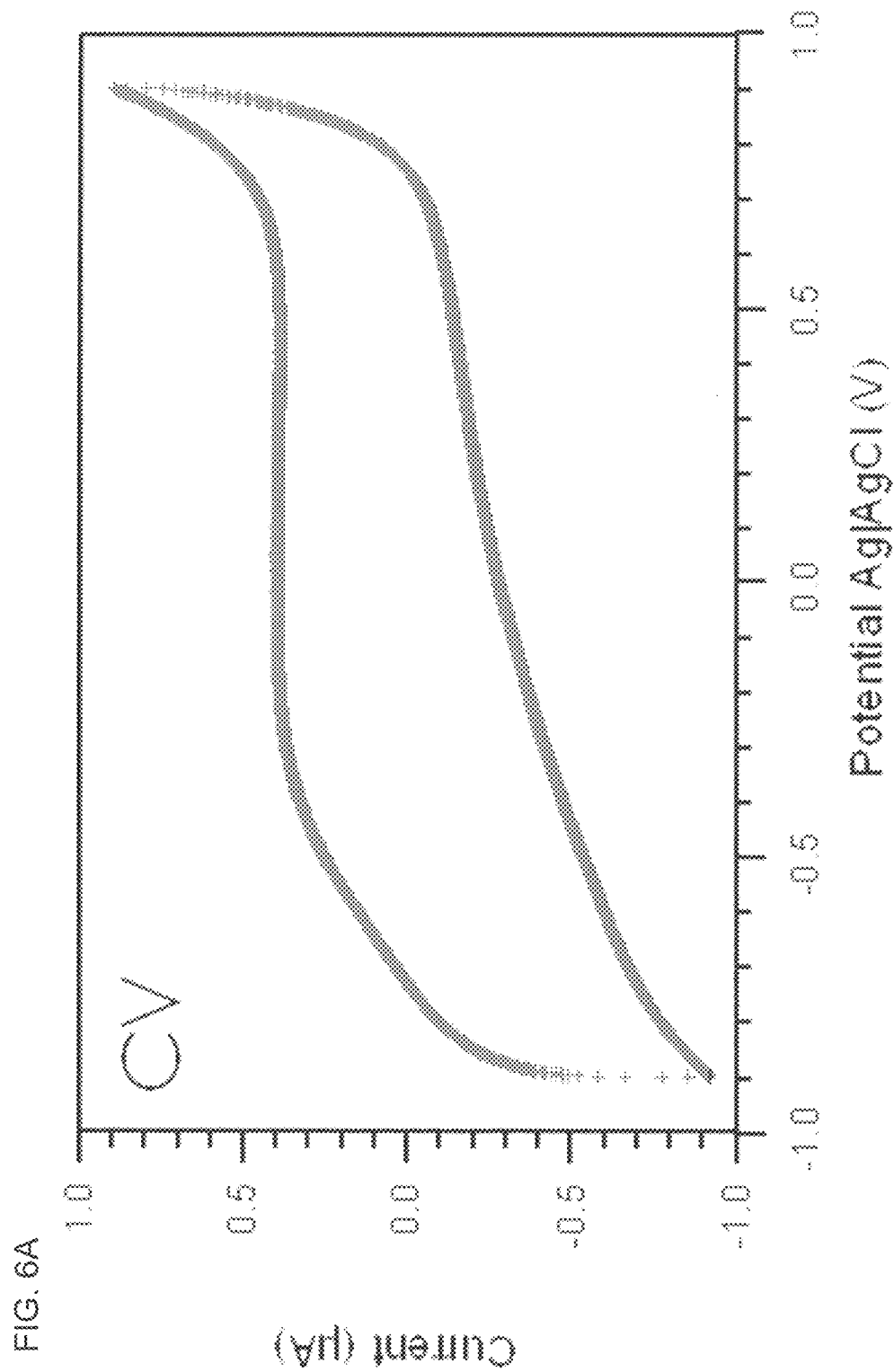

BIO-ELECTRONIC DEVICES INCLUDING HYDROLYTICALLY STABLE POLYMERS

CROSS-REFERENCE TO RELATED APPLICATION

This application is a continuation of U.S. non-provisional application Ser. No. 16/677,243, filed by Walter Voit, et al. on Nov. 7, 2010, entitled "HYDROLYTICALLY STABLE POLYMERS, METHOD OF SYNTHESIS THEREOF AND USE IN BIO-ELECTRONIC DEVICES," which claims the benefit of U.S. Provisional Application Ser. No. 62/760,582, filed by Walter Voit, et al. on Nov. 13, 2018, entitled "HYDROLYTICALLY STABLE POLYMERS, METHOD OF SYNTHESIS THEREOF AND USE IN BIO-ELECTRONIC DEVICES," commonly assigned with this application and incorporated herein by reference in its entirety.

TECHNICAL FIELD

This application is directed, in general, to hydrolytically stable shape memory polymers, and more specifically, thiol-ene shape memory polymers with ester-free backbones, methods of synthesis thereof, and, the inclusion of such polymers in bio-electronic devices

BACKGROUND

The use of chronically implanted bio-electronic devices can sometimes be hampered by a failure over time in the device's ability to record and/or stimulate neural signals. Various reasons suggested for this failure include neuroinflammatory responses, device failure, or chronic damage to surrounding tissue. Some forms of device failure have been attributed to large, orders of magnitude, higher elastic modulus of some device substrates as compared to living tissue.

There is growing interest in the use of shape memory polymers (SMPs) as materials in bio-electronic devices for neural recording and stimulating electrodes, such as nerve cuffs, spinal cord stimulators, brain probes, and electrode grids. These materials exhibit a thermal induced change in elastic modulus which can give them the ability to undergo softening after insertion in the body, and therefore reduce the mismatch in modulus that usually exists between the device and the tissue and thereby mitigate device failure. However, there is an on-going need for devices containing such polymers to remain mechanically stable for extended periods of implantation.

SUMMARY

The present disclosure provides in one embodiment, a thiol-ene shape memory polymer including a sequential chain of a first type of monomer covalently bonded to a second type of monomer via thiol-ene linkages that form a backbone of the polymer. The first type of monomer includes two or more thiol functional groups and the second type of monomer includes two or more alkene functional groups. The sequential chain of the covalently bonded first and second types of monomers forming the polymer backbone is free of ester groups.

Another embodiment is a method of synthesizing a thiol-ene shape memory polymer. The method includes forming a monomer mixture that includes a first type of monomer and a second type of monomer. The first type of monomer includes two or more thiol functional groups and the second type of monomer includes two or more alkene functional groups. The method also includes adding a photo-initiate-able catalytic agent to the monomer mixture to form a reaction mixture and photo-initiating the photo-initiate-able catalytic agent to form a free radical catalyst to thereby initiate step-growth polymerization of the first types of monomer with the second types of monomers to form a sequential chain of the first types of monomers covalently bonded to the second types of monomers via thiol-ene linkages that form a backbone of the polymer. The sequential chain of the covalently bonded first and second types of monomers forming the polymer backbone is free of ester groups.

Still another embodiment is a bio-electronic device, the device including a substrate layer composed of the thiol-ene shape memory polymer.

Yet another embodiment is a method of manufacturing a bio-electronic device. The method includes providing a base layer and depositing the reaction mixture on the base layer. The method also includes photo-initiating the photo-initiate-able catalytic agent to form a free radical catalyst to initiate step-growth polymerization of the first types of monomers with the second types of monomers to form a sequential chain of the first type of monomers covalently bonded to the second type of monomers via thiol-ene linkages that form a backbone of the polymer to thereby form a thiol-ene shape memory polymer substrate layer. The sequential chain of the covalently bonded first and second types of monomers forming the polymer backbone is free of ester groups.

BRIEF DESCRIPTION OF FIGURES

For a more complete understanding of the present disclosure, reference is now made to the following detailed description taken in conjunction with the accompanying Figures, in which:

FIGS. 5A-5L schematically illustrates steps in an example bio-electronic device fabrication process of the disclosure;

FIG. 6A presents example cyclic voltammetry (CV) results obtained for an example bio-electronic device of disclosure.

DETAILED DESCRIPTION

Figure 1A:
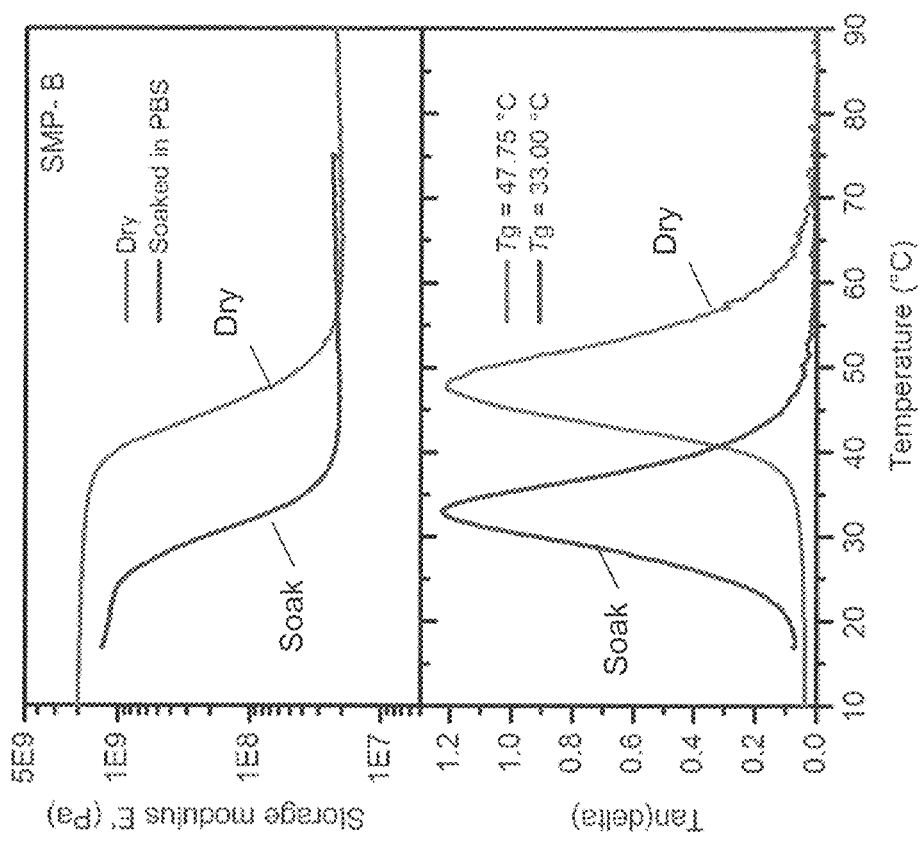
FIG. 1A presents example dynamic mechanical analysis data for samples of SMP-A showing changes in the storage modulus (top) and tan delta (bottom) as a function of temperature with the polymer samples in a dry state (Dry) and after exposure to phosphate buffered saline (PBS).

As part of the present invention we recognized that some current SMP formulations, such as used in implanted bio-electronic devices, often contain ester groups within the main backbone chain of the polymer, and because these ester groups are prone to hydrolytic decomposition under physiological conditions, the time-frame for chronic in vivo implantation is more limited than desired.

Herein we disclose our development of thiol-ene based SMPs with ester-free backbones and demonstrate that such SMPs are more resistant to hydrolytic degradation than analogous SMPs with ester-containing backbones. The thiol-ene polymers disclosed herein are suitable materials as substrate and/or encapsulation layers of chronically implanted bio-electronic devices which we believe could advantageously remain stable in vivo for long periods of time (e.g., several months or years).

One embodiment of the disclosure is a thiol-ene shape memory polymer. The polymer includes a sequential chain of a first type of monomer covalently bonded to a second type of monomer via thiol-ene linkages that form a backbone of the polymer. The first type of monomer (e.g., each of the first monomer types) includes two or more thiol functional groups and the second type of monomer (e.g., each of the second monomer types) includes two or more alkene functional groups. The sequential chain of the covalently bonded first and second types of monomers forming the polymer backbone is free of ester groups.

The term "polymer backbone" as used herein refers to the sequential chain of the covalently bonded repeating units of first and second types of the polymer. The longest continuous line which can be hypothetically drawn through the covalent bonds connecting the atoms in the repeating units of the polymer, without doubling back or returning, will in general constitute the "backbone" of the polymer. As would be understood by one skilled in the pertinent art, the polymer backbone does not include terminal functional groups at each end of the backbone or pendant functionalized side chains spaced along the polymer backbone.

Thus, as further disclosed below, while the sequential chain of repeating monomer units corresponding to the backbone chain of the disclosed thiol-ene SMPs contains no ester groups, some embodiments of the thiol-ene SMPs can have at least some pendant side chains having ester groups while other embodiments of the thiol-ene SMPs can have pendant side chains that have no ester groups.

In some embodiments of the thiol-ene SMP, the first and second types of monomers are free of ester groups. That is, neither the polymer backbone nor pendant side chains have any ester groups. For instance, in such embodiments, the first and second types of monomer do not include an acrylate functional group where the acrylate functional group includes a vinyl group directly attached to the carbonyl carbon of an ester group. In some such embodiments, for example, the first type of monomer only has thiol functional groups and the second type of monomer only has alkene functional groups. That is, only thiol functional groups and alkene functional groups of the first and second types of monomers, respectively, are available for participation in the thiol-click polymerization mechanism resulting in the thiol-ene SMP.

In some embodiments, e.g., to facilitate simplifying the design and tuning of the thermal induced change in elastic modulus of the SMP to a desirable range, the first type of monomer is free of alkene, acrylate, isocyanate or other functional groups that could react with an alkene functional group, and, the second type of monomer is free of thiol acrylate, isocyanate or other functional groups that could react with a thiol functional group.

Non-limiting examples of the first type of monomer having two or more thiol functional groups and no alkene or acrylate functional groups include: 1,3,5-tris(3-mercaptopropyl)-1,3,5-triazinane-2,4,6-trione (TTTSH) and or 1,10-decanedithiol (DDT), 1,2-Ethanedithiol, 1,3-Propanedithiol, 1,4 butanedithiol, 1,5-Pentanedithiol, 1,6-Hexanedithiol, 1,7-Heptanedithiol, 1,8-Octanedithiol, 1,9-Nonanedithiol, 1,11-Undecanedithiol, 1,12-Dodecanedithiol, 1,13-Tridecanedithiol, 1,14-Tetradecanedithiol, 1,15-Pentadecanedithiol, 1,16-Hexadecanedithiol, 2,2'-(Ethylenedioxy)diethanethiol, Tetra(ethylene glycol) dithiol, Hexa(ethylene glycol) dithiol; dithiotricyclodecane, or combinations thereof.

Non-limiting examples of the second type of monomer having two or more alkene functional groups and no thiol or acrylate functional groups include 1,3,5-triallyl-1,3,5-triazine-2,4,6-trione (TATATO), 2,4,6-Triallyloxy-1,3,5-triazine, 2,4,6-tris(2-allyloxy)ethoxy)-1,3,5-triazine (TAET), 1,2,4-Trivinylcyclohexane, Trimethylolpropane triallyl ether, Dicyclopentadiene, Trimethylolpropane diallyl ether, Diallyl ether, or combinations thereof.

Any embodiments of the thiol-ene SMP include sequential chains of the first type of monomer covalently bonded to the second type of monomer in stoichiometric amount such that the mole fraction of the thiol functional groups of the first monomer is substantially equal to (e.g., within 90% or in some embodiments within 99%) the mole fraction of the alkene and/or acrylate functional groups of the second monomer. As an example, for some embodiments, mole fractions of the first type of monomers of 1,10-decanedithiol, and 1,3,5-tris(3-mercaptopropyl)-1,3,5-triazinane-2,4, 6-trione, and, second type of monomers of 1, 3, 5-triallyl-1, 3, 5-triazine-2, 4, 6-trione present in the sequential chain, equal about 0.2 to 0.12, about 0.3 to 0.38, and about 0.5, respectively. As another example, for some embodiments, the first type of monomer is 1,3,5-tris(3-mercaptopropyl)-1, 3,5-triazinane-2,4,6-trione (TTTSH), and, the second types of monomers are a mixture of 1,3,5-triallyl-1,3,5-triazine-2,4,6-trione (TATATO) and 2,4,6-tris(2-allyloxy)ethoxy)-1, 3,5-triazine (TAET). In some such embodiments, mole fractions of the TTTSH, the TATATO and the TAET present in the sequential chain equal about 0.5, about 0.005 to 0.495, and about 0.005 to 0.495, respectively. In some such embodiments, mole fractions of the TTTSH, the TATATO and the TAET present in the sequential chain equal about 0.5, about 0.25 to 0.45, and about 0.05 to 0.25, respectively.

In some embodiments of the thiol-ene SMP, the first type of monomer can include a 1,n alkanedithiol having a chemical formula of $HS-(CH_2)_n-SH$ where n has a integer value in a range from 4 to 14, and also includes a di- or tri-mercaptoalkyl substituted triazinane having a chemical formula of:

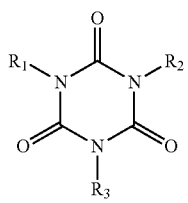

where at least two of $R_1$, $R_2$, and $R_3$, include a thiol functional group and third one of $R_1$, $R_2$, and $R_3$, optionally may include a thiol functional group.

As a non-limiting example, for some embodiments of a tri-mercaptoalkyl substituted triazinane first monomer, $R_1$ has a chemical formula of —$(CH_2)o_1SH$, where $o_1$ has an integer value in a range from 2 to 8, $R_2$ has a chemical formula of —$(CH_2)o_2SH$, where $o_2$ has an integer value in a range from 2 to 8, and $R_3$ has a chemical formula of —$(CH_2)o_3SH$, where $o_3$ has an integer value in a range from 2 to 8. In some such embodiments, $o_1$, $o_2$, and $o_3$, all have a same integer value in a range from 1 to 8, while in other embodiments, $o_1$, $o_2$, and $o_3$, can have independently different integer values in this range.

For example, in some embodiments, the first type of monomer includes the alkanedithiol having a formula of $HS$—$(CH_2)_n$—$SH$ where n has a integer value in a range from 8 to 12, and also includes the tri-mercaptoalkyl substituted triazinane having a formula of:

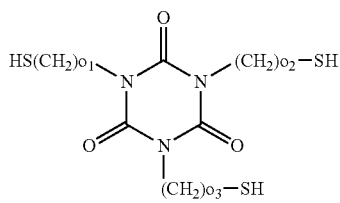

where $o_1$, $o_2$, and $o_3$ each independently have an integer value in a range from 2 to 5.

As a non-limiting example, for some embodiments of a di-mercaptoalkyl substituted triazinane first monomer, $R_1$ and $R_2$ have the same chemical formula as described above and $R_3$ has a chemical formula of —$(CH_2)o_3R_4$ where $o_3$ has an integer value in a range from 1 to 8 and $R_4$ is one of H or $CH_3$. In some such embodiments, $o_1$, $o_2$, and $o_3$, all have a same integer value in a range from 1 to 8, while in other embodiments, $o_1$, $o_2$, and $o_3$, can have independently different integer values in this range.

For example, for any such embodiments, the second type of monomer can include a di- or tri-alkene alkyl substituted triazinane having a chemical formula of:

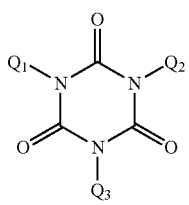

where at least two of $Q_1$, $Q_2$, and $Q_3$, include an alkene functional group and third one of $Q_1$, $Q_2$, and $Q_3$, optionally may include an alkene functional group.

As a non-limiting example, for some embodiments of a tri-alkene alkyl substituted triazinane second monomer, $Q_1$ has a chemical formula of —$(CH_2)p_1C$=$CH_2$, where $p_1$ has an integer value in a range from 1 to 8, $Q_2$ has a chemical formula of —$(CH_2)p_2C$=$CH_2$, where $p_2$ has an integer value in a range from 1 to 8, and $Q_3$ has a chemical formula of —$(CH_2)p_3C$=$CH_2$, where $p_3$ has an integer value in a range from 1 to 8. In some such embodiments, $p_1$, $p_2$, and $p_3$, all have a same integer value in a range from 1 to 8, while in other embodiments, $p_1$, $p_2$, and $p_3$, can have independently different integer values in this range.

As a non-limiting example, for some embodiments of a di-alkene alkyl substituted triazinane second monomer, $Q_1$ and $Q_2$ has the same chemical formula as described above, and $Q_3$ has a chemical formula of —$(CH_2)p_3R_6$ where $p_3$ has an integer value in a range from 1 to 8 and $R_6$ is one of H, or $CH_3$. In some such embodiments, $p_1$, $p_2$, and $p_3$, all have a same integer value in a range from 1 to 8, while in other embodiments, $p_1$, $p_2$, and $p_3$, can have independently different integer values in this range.

For example, in some embodiments, the alkene alkyl substituted triazinane second monomer has a chemical formula of:

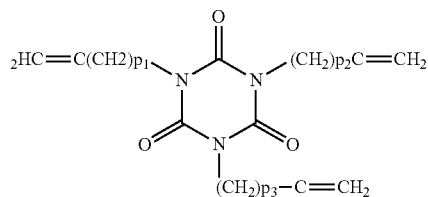

where $p_1$, $p_2$, and $p_3$ each independently have an integer value in a range from 2 to 5.

As discussed above, for some embodiments of the thiol-ene SMP, one or both of the first or second types of monomers can include an ester functional group, where the ester functional group is located as a pendant group in a side chain covalently bonded to the sequential chain of repeating units of the first and second monomers of the polymer. As further disclosed below, in some embodiments, the ester functional group of the first or second monomer can be part of an acrylate functional group.

Having such an ester-containing functional group in a pendant side chain of thiol-ene SMP may advantageously allow the thiol-ene SMP to carry a chemical agent which can then be released, via hydrolysis of the ester, in the vicinity of an in vivo implanted bio-electronic device that includes such a thiol-ene SMP. A chemical agent with anti-inflammatory properties or immuno-suppressing properties, when released from the thiol-ene SMP via hydrolysis of the ester bond after implantation in living tissue, could help mitigate the tissue's inflammatory response associated with surgery and/or implantation in the vicinity of the implantation. Non-limiting examples of such agents include: melatonin, curcumin, pycnogenol, Vitamin E succinate, bovine serum albumin, and triazoles. One skilled in the pertinent art would understand how such agents could be bonded to an ester or acrylate containing functional group of the first or second type of monomers.

In some such embodiments of the thiol-ene SMP, the first type of monomer and/or the second type of monomer can include an acrylate functional group. The two or more thiol functional groups of the first type of monomer and the two or more alkene functional groups of the second type of monomer participate in the thiol click polymerization to form the thiol-ene SMP while the acrylate functional group is in a pendant side chain of the thiol-ene SMP. For instance, in some such embodiments, the first type of monomer only has thiol functional groups and the second type of monomer has two of more alkene functional groups and at least one acrylate functional group. For instance, in some such embodiments, the first type of monomer has two or more thiol functional groups the second type of monomer only has alkene functional groups.

Non-limiting examples of the second type of monomer having at least two alkene functional groups and at least one acrylate functional group includes: 1,3,5-Triacryloylhexahydro-1,3,5-triazine 4,6-bis(allyloxy)-1,3,5-triazin-2-yl acrylate; 2-(3,5-bis(2-(allyloxy)ethyl)-2,4,6-trioxo-1,3,5-triazinan-1-yl)ethyl acrylate; 3,5-bis (allyloxy)phenyl acrylate; or combinations thereof.

As another non-limiting example, for some embodiments of a di-mercaptoalkyl substituted triazinane first monomer, $R_3$ has a chemical formula of $-(CH_2)_{o_3}R_4$ where $o_3$ has an integer value in a range from 1 to 8 and $R_4$ is $-O-CO-R_5$, where $R_5$ is an anti-inflammatory agent or drug agent. Additionally or alternatively, for some embodiments of di-alkene alkyl substituted triazinane second monomer, $Q_3$ has a chemical formula of $-(CH_2)_{p_3}R_6$ where $p_3$ has an integer value in a range from 1 to 8 and $R_6$ is $-O-CO-R_7$, where $R_7$ is the anti-inflammatory agent or the drug agent or a different anti-inflammatory agent or the drug agent.

As another non-limiting example, in some embodiments of the thiol-ene SMP, one or both of the first and second types of monomers can be a substituted Trimethylolpropane tris having a chemical formula of:

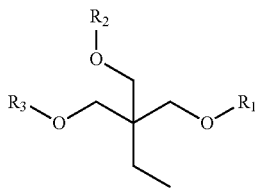

where, for the first type of monomer, at least two of $R_1$, $R_2$, or $R_3$ are or include a 3-mercaptopropionate functional group having the chemical formula of:

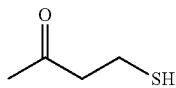

and, for the second type of monomer, at least two of $R_1$, $R_2$, or $R_3$ are or include an allyl functional group having the chemical formula:

In some such embodiments, for the first type of monomer, two of $R_1$, $R_2$, or $R_3$ can be the 3-mercaptopropionate functional group and the other one of $R_1$, $R_2$, or $R_3$ has a chemical formula of $-(CH_2)_{q_1}R_8$ where $q_1$ has an integer value in a range from 1 to 8 and $R_8$ includes an ester having a chemical formula of $-O-CO-R_{10}$, where $R_{10}$ is an anti-inflammatory agent or a drug agent. Additionally or alternatively, for the second type of monomer, two of $R_1$, $R_2$, or $R_3$ can be or include the allyl functional group and the other one of $R_1$, $R_2$, or $R_3$ has the chemical formula of $-(CH_2)_{q_2}R_9$ where $q_2$ has an integer value in a range from 1 to 8 and $R_9$ includes an ester having a chemical formula of $-O-CO-R_{11}$, where $R_{11}$ is the anti-inflammatory agent or the drug agent or a different anti-inflammatory agent or drug agent.

Based on the present disclosure, one skilled in the pertinent art would appreciate how other embodiments of the thiol-ene SMP could be synthesized to include ester-containing pendant side chains and how various types of in vivo releasable anti-inflammatory, drug or other chemical agents could be bonded to such pendant side chains.

Another embodiment of the disclosure is a method of synthesizing a thiol-ene SMP.

Embodiments of the method include forming a monomer mixture of a first type of monomer and a second type of monomer (e.g., a mixture of mutually miscible liquids of the monomers in a solvent-free mixture). The first type of monomer (e.g., each of the first monomer types) includes two or more thiol functional groups and the second type of monomer (e.g., each of the second monomer types) includes two or more alkene functional groups.

The method includes adding a photo-initiate-able catalytic agent to the monomer mixture to form a reaction mixture, and, photo-initiating the photo-initiate-able catalytic agent to form a free radical catalyst. The free radical catalyst initiates step-growth polymerization of the first types of monomer with the second types of monomers to form a sequential chain of the first types of monomers covalently bonded to the second types of monomers via thiol-ene linkages that form a backbone of the polymer, where the sequential chain of the covalently bonded first and second types of monomers forming the polymer backbone is free of ester groups.

The method of synthesis can be used to synthesize any of the thiol-ene SMPs disclosed herein. For instance, in some embodiments, the first and second types of monomers are free of ester groups, resulting in a polymer that is likewise free of ester groups, e.g., both the backbone and pendent side chains of the polymer have no ester groups, while in other embodiments, one or both of the first and second types of monomers include ester groups, resulting in a polymer with ester group-containing pendent side chains.

In some embodiments of the method, the photo-initiate-able catalytic agent includes at least one of: 2,2-Dimethoxy-2-phenylacetophenone (DMPA; also referred to herein as 2,2-Dimethoxy-1,2-diphenylethan-1-one, Irgacure 651); 1-Hydroxy-cyclohexyl-phenyl-ketone (Irgacure 184); Bis(2,4,6-trimethylbenzoyl)-phenylphosphineoxide (Irgacure 819); 2,4,6-Trimethylbenzoyl-diphenyl-phosphineoxide (Darocure TPO); 2-Methyl-4'-(methylthio)-2-morpholino-propiophenone (Irgacure 907); 2-Benzyl-2-dimethylamino-1-(4-morpholinophenyl)-butanone-1 (Irgacure 369); Methyl benzoylformate (Darocur MBF); Benzophenone (Darocur BP), or combinations thereof, e.g., Irgacure 500 (Irgacure184+ Darocur BP); Irgacure 1300 (Irgacure 369+Irgacure 651); Darocur 4265 (Darocur TPO+Darocur 1173).

In some embodiments of the method, the photo-initiate-able catalytic agent added to the mixture has a concentration in the reaction mixture that is in a range from about 0.01 wt % to 1 wt % relative to the total weight of the first and second types of monomers in the reaction mixture. For instance, in some embodiments, the concentration of photo-initiate-able catalytic agent is in a range from 0.01 to 0.2 wt %, and more preferably from 0.09 to 0.11 wt %, In some embodiments the concentration of photo-initiate-able catalytic agent is in a range from 0.2 to 0.3 wt %, 0.4 to 0.5 wt %, 0.5 to 0.6 wt %, 0.6 to 0.7 wt %, 0.7 to 0.8 wt %, 0.8 to 0.9 wt %, or 0.9 to 1 wt %.

Another embodiment of the disclosure is a bio-electronic device. The device includes a substrate layer composed of a thiol-ene SMP, such as any of the thiol-ene SMP embodiments disclosed herein.

For instance, the thiol-ene SMP substrate layer includes a sequential chain of a first type of monomer covalently bonded to a second type of monomer via thiol-ene linkages that form a backbone of the polymer. The first type of monomer includes two or more thiol functional groups and the second type of monomer includes two or more alkene functional groups. The sequential chain of the covalently bonded first and second types of monomers forming the polymer backbone is free of ester groups.

As further disclosed in the experimental results section to follow, embodiments of the device can further include at least one patterned gold interconnect line adhered to the substrate layer, a TiN electrode layer on a portion of the at least one gold interconnect line and a second substrate layer composed of the thiol-ene SMP, covering the substrate layer and the gold interconnect lines and having an opening therein, the TiN electrode layer exposed through the opening. Some embodiments of the device can include a sputtered iridium oxide (SIROF) or platinum electrode layer.

Embodiments of the bio-electronic device can be configured as implantable devices for humans or other species, for neural recording and stimulation, such as, but not limited to, cortical probes, nerve cuffs, blanket probes, grid electrodes, or spinal cord stimulators.

Another embodiment of the disclosure is a method of manufacturing a bio-electronic device, such as any of the bio-electronic devices disclosed herein.

The method includes providing a base layer (e.g., glass substrate or a silicon wafer layer) and depositing a reaction mixture on the base layer. The reaction mixture includes a first type of monomer, a second type of monomer and a photo-initiate-able catalytic agent. The first type of monomer includes two or more thiol functional groups and the second type of monomer includes two or more alkene functional groups.

The method also includes photo-initiating the photo-initiate-able catalytic agent to form a free radical catalyst. The catalyst initiates the step-growth polymerization of the first types of monomers with the second types of monomers to form a sequential chain of the first type of monomers covalently bonded to the second type of monomers via thiol-ene linkages that form a backbone of the polymer, to thereby form a thiol-ene SMP substrate layer. The sequential chain of the covalently bonded first and second types of monomers that forms the polymer backbone is free of ester groups.

As further disclosed in the experimental results section to follow, embodiments of the method can further include forming a patterned gold interconnect line adhered to the substrate layer, forming a TiN electrode layer on a portion of the gold interconnect line, depositing a second substrate layer composed of the thiol-ene SMP, the second substrate layer covering the thiol-ene SMP substrate layer and the gold interconnect lines, and forming an opening in the second substrate layer, wherein the TiN electrode layer is exposed through the opening.

To facilitate understanding of various features of the disclosure, selected structures and acronyms of some of the example monomers and photolatent bases referred to in the text and figures are presented below:

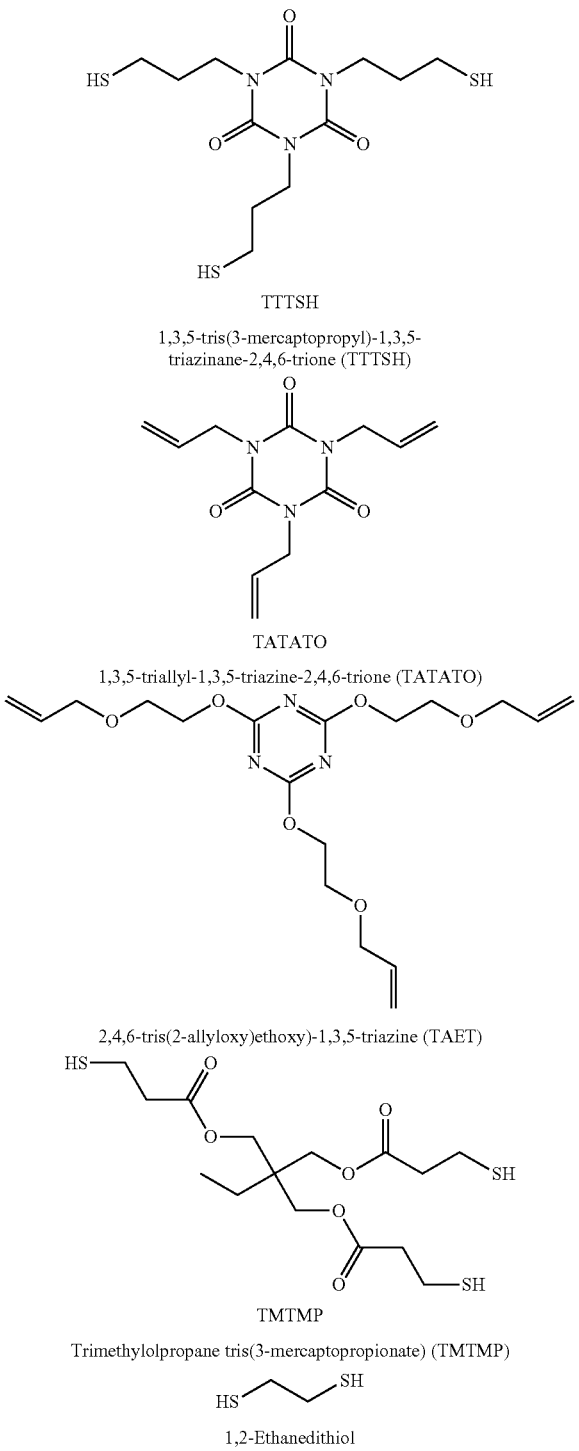

TTTSH
1,3,5-tris(3-mercaptopropyl)-1,3,5-triazinane-2,4,6-trione (TTTSH)

TATATO
1,3,5-triallyl-1,3,5-triazine-2,4,6-trione (TATATO)

2,4,6-tris(2-allyloxy)ethoxy)-1,3,5-triazine (TAET)

TMTMP
Trimethylolpropane tris(3-mercaptopropionate) (TMTMP)

1,2-Ethanedithiol

-continued

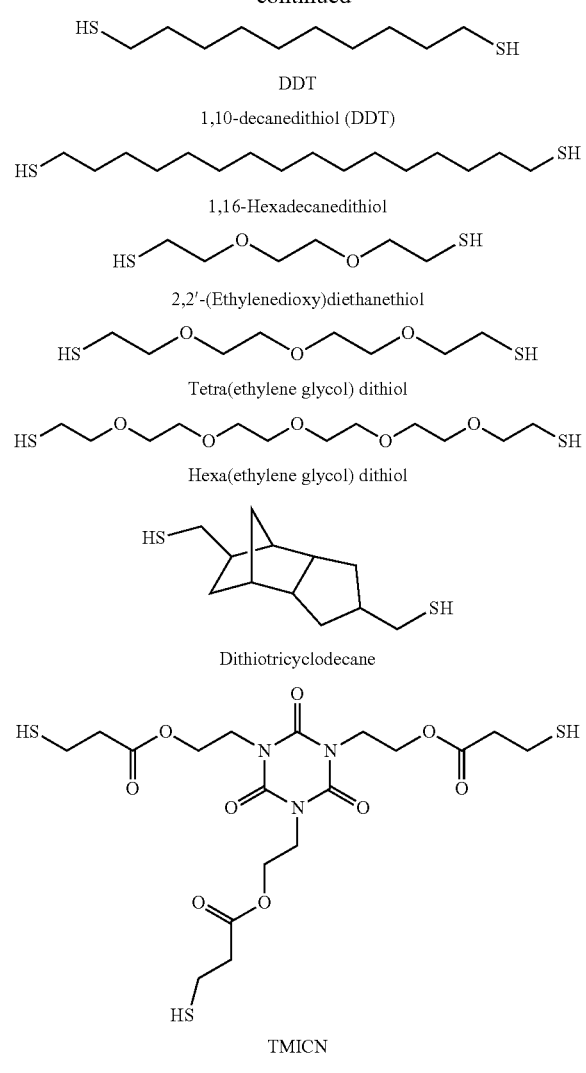

1,10-decanedithiol (DDT)

1,16-Hexadecanedithiol 2,2'-(Ethylenedioxy)diethanethiol

Tetra(ethylene glycol) dithiol

Hexa(ethylene glycol) dithiol

Dithiotricyclodecane

Tris [2-(3-mercaptopionyloxy) ethyl] isocyanurate (TMICN)

1,3,5-Triacryloylhexahydro-1,3,5-triazine 2,4,6-Triallyloxy-1,3,5-triazine

-continued

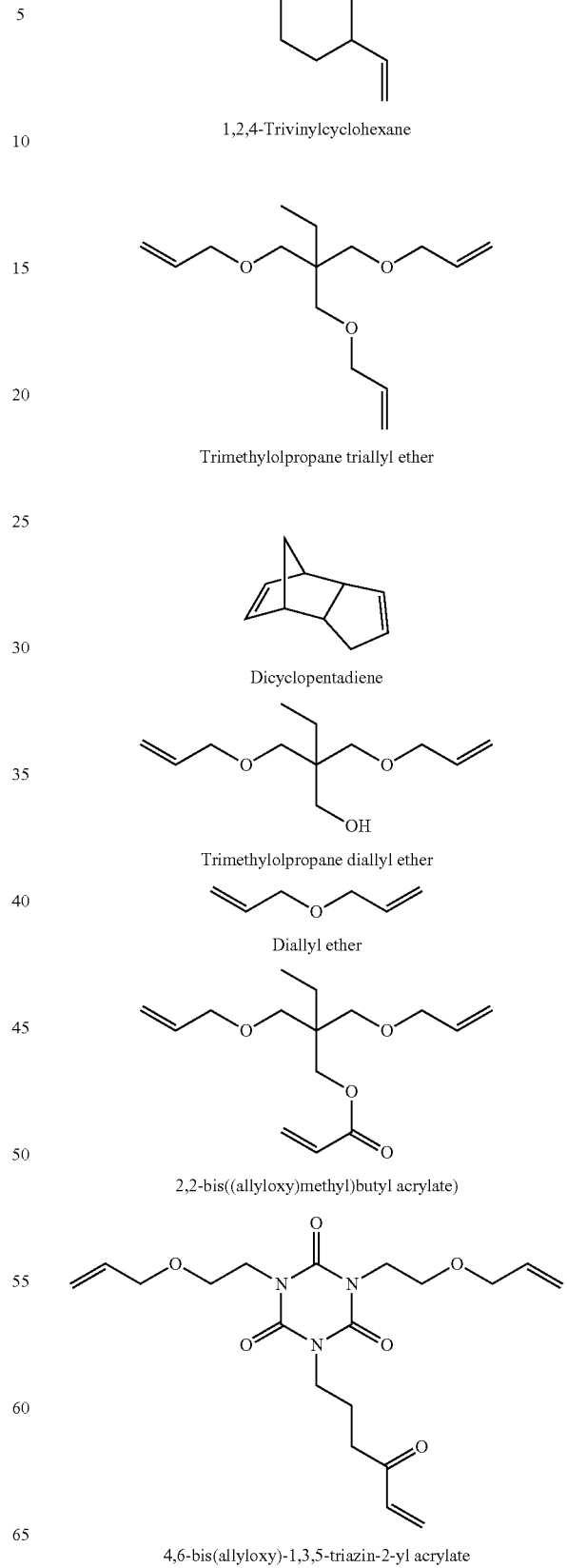

1,2,4-Trivinylcyclohexane

Trimethylolpropane triallyl ether

Dicyclopentadiene

Trimethylolpropane diallyl ether

Diallyl ether 2,2-bis((allyloxy)methyl)butyl acrylate)

4,6-bis(allyloxy)-1,3,5-triazin-2-yl acrylate

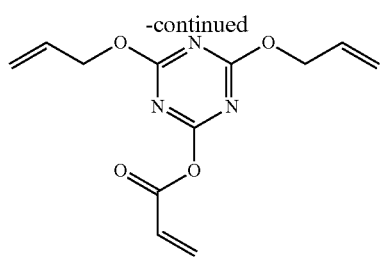

2-(3,5-bis(2-(allyloxy)ethyl)-2,4,6-trioxo-1,3,5-triazinan-1-yl)ethyl acrylate

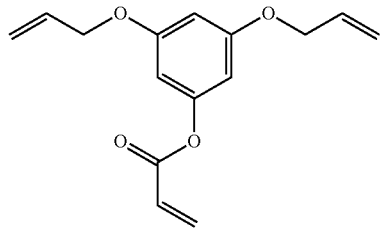

3,5-bis(allyloxy)phenyl acrylate

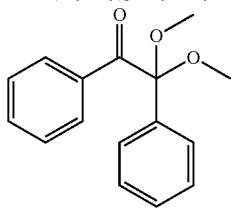

2,2-Dimethoxy-2-phenylacetophenone (DMPA, also referred to as 2,2-Dimethoxy-1,2-diphenylethan-1-one, Irgacure 651)

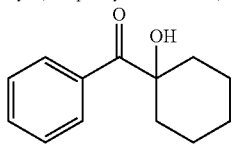

1-Hydroxy-cyclohexyl-phenyl-ketone (Irgacure 184)

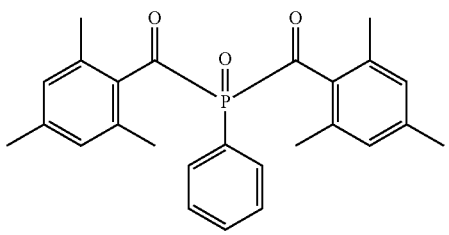

Bis(2,4,6-trimethylbenzoyl)-phenylphosphineoxide (Irgacure 819)

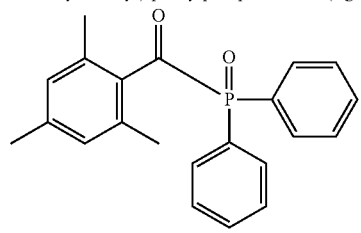

2,4,6-Trimethylbenzoyl-diphenyl-phosphineoxide (Darocure TPO)

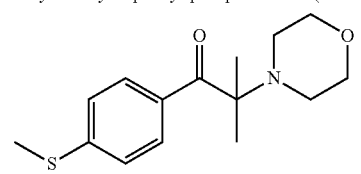

2-Methyl-4'-(methylthio)-2-morpholinopropiophenone (Irgacure 907)

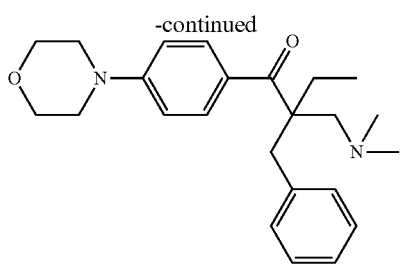

2-Benzyl-2-dimethylamino-1-(4-morpholinophenyl)-butanone-1 (Irgacure 369)

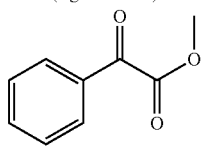

Methyl benzoylformate (Darocure MBF)

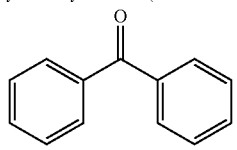

Benzophenone (Darocur BP)

Experimental Results

To further illustrate various features of the disclosure, the synthesis of non-limiting example hydrolytically stable polymers and some of their physical and mechanical, aging and cytotoxicity properties are presented below.

These results demonstrate that the thermomechanical properties of thiol-ene SMPs with ester-free backbones are highly tunable with various degrees of softening under physiological relevant conditions including implantation into the body. Additionally, we demonstrate that such polymers are biocompatible and do not have negative effects on cell viability and they can be sterilized without changing their softening capabilities. Also, the experimental results from accelerated aging studies suggest that such SMPs have the potential to remain stable in the human seven years without signs of substantial degradation.

Synthesis of a First Type of Monomer Having Three Thiol Functional Groups, 1,3,5-tris(3-mercaptopropyl)-1,3,5-triazinane-2,4,6-trione (TTTSH)

A mixture of 30 g (120.4 mmol) 1, 3, 5-triallyl-1, 3, 5-triazine-2, 4, 6-trione (TATATO), 82.40 g (1080 mmol) thioacetic acid, and 1.98 g (12.04 mmol) 2, 2'-azobis (2-methylpropionitrile) (AIBN) were placed in a 500-mL three-neck round-bottom flask which was equipped with condenser and nitrogen inlets. This reaction mixture was stirred at 65° C. for 24 h under a nitrogen atmosphere. Excess thioacetic acid was removed by reducing the pressure in the flask. The reaction mixture was reacted with methanol (100 ml) and concentrated hydrochloric acid (50 ml) at 65° C. for 36 h to cleave the thioester bond. After cooling down to room temperature, water was added (300 ml) to the reaction mixture and extracted three times with methylene chloride (300 ml). The reaction mixture was then washed with sodium hydrogen carbonate solution (5%), dried over MgSO$_4$, and concentrated with reduced pressure.

In some embodiments the reaction mixture was purified by column chromatography using an eluant gradient of hexane: ethyl acetate mixtures 1:0 to 1:4 to obtain TTTSH as a yellowish viscous liquid.

Synthesis of a Thiol-Ene Polymer with an Ester-Free Backbone (SMP-A) and an Analog Thiol-Ene Polymer with an Ester-Containing Backbone (SMP-B)

Starting materials included: 1,3,5-Triallyl-1,3,5-triazine-2,4,6(1H,3H,5H)-trione (TATATO), Trimethylolpropane tris (3-mercaptopropionate) (TMTMP), photoinitiator 2,2-Dimethoxy-2-phenylacetophenone (DMPA) purchased from Sigma Aldrich, Tris [2-(3-mercaptopropionyloxy) ethyl] isocyanurate (TMICN) purchased from Evans Chemicals, and 1,10-decanedithiol (DDT). All chemicals were used as received without further purification. TTTSH was synthesized as described above.

Reactant mixtures to form SMP-A and SMP-B both contained stoichiometric quantities of thiol- to -ene functional groups. Mole fractions of reactant mixtures for SMP-A were TTTSH:DDT:TATATO equal to 0.3:0.2:0.5, respectively. Mole fractions of reactant mixtures for SMP-B were TMTMP:TMICN:TATATO equal to 0.45:0.05:0.5, respectively. About 0.1 wt % DMPA of the total monomer weight was dissolved in the reactant mixture solutions. The vessel containing the reactant mixture solutions were covered in aluminum foil to prevent incident light from contacting the solution, the solutions were mixed by planetary speed mixing and kept at room temperature.

The reactant mixture solutions for SMP-A and SMP-B were spin cast on 75 mm×50 mm base layer glass microscope slides using a Laurell WS-650-8B spin coater. The spin speed was 350 rpm and spin time was 45 s for SMP-A and 600 rpm and 25 s for SMP-B, respectively, to form polymer layers having a thickness of about 30 μm. Polymerization was performed at ambient temperature using an UVP CL-1000 crosslinking chamber with five overhead 365 nm UV bulbs for 60 minutes under air to initiate photopolymerization of the monomers in the solution and form the polymers. Samples of the polymers were then placed in a vacuum oven at 120° C. and 5 mmHg for 24 h to complete the polymerization to form SMP-A and SMP-B.

Dynamic Mechanical Analysis

Figure 1B:
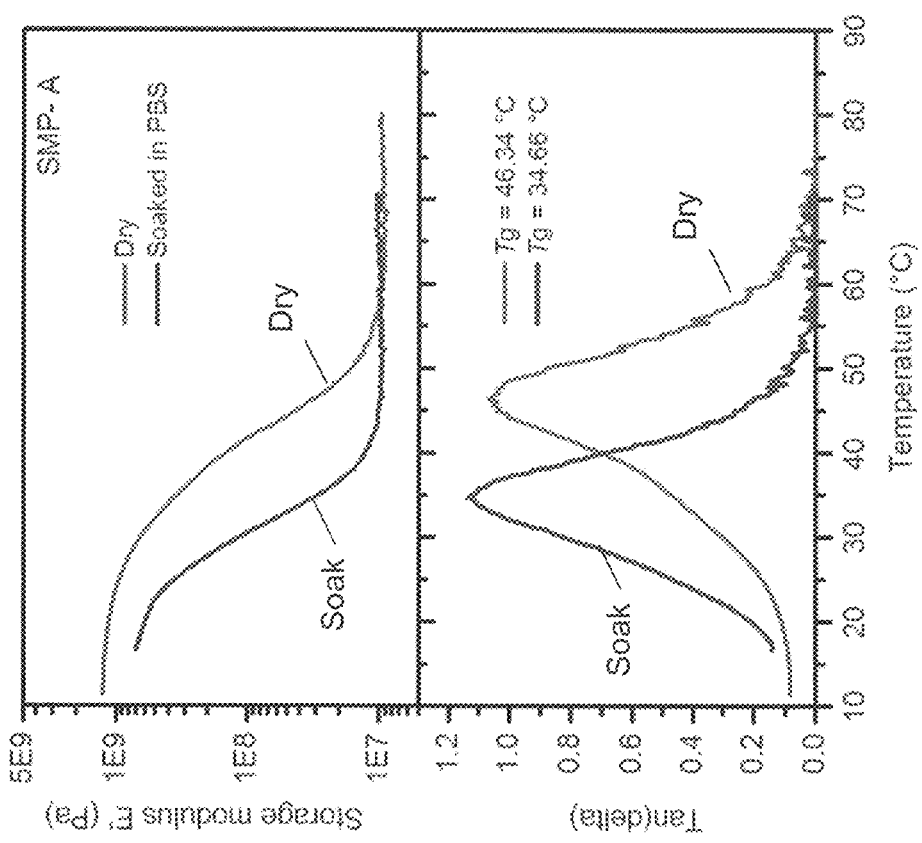
FIG. 1B presents example dynamic mechanical analysis data for samples of SMP-B showing changes in the storage modulus (top) and tan delta (bottom) as a function of temperature with the polymer sample in a dry state (Dry) and after softening the polymer in phosphate buffered saline (PBS)

To mimic the effect of body fluids on mechanical properties, dynamic mechanical analysis of SMP-A and SMP-B was performed in dry and soaked conditions (FIGS. 1A and 1B). The glass transition temperature (Tg) and storage modulus (E') of SMP-A in the glassy and rubbery state was similar to SMP-B. Soaked conditions were achieved by immersing the polymers in phosphate buffered saline (PBS) and monitoring the storage modulus loss until the modulus no longer decreased. Soaking in PBS resulted in a storage modulus decrease for SMP-A from 935 MPa at room temperature to 22 MPa after 20 min at 37° C. In comparison, under these same conditions the storage modulus of SMP-B dropped from 1740 to 30 MPa. After soaking in PBS, the glass transition temperatures of SMP-A and SMP-B both decreased by about 12 to 14° C. as compared to their respective dry values. For instance, for samples of SMP-A, Tg decreased from about 46.3 to about 34.6° C. and for samples of SMP-B, Tg decreased from about 47.75 to about 33.0° C.

Accelerating Aging Tests

Figure 2B:
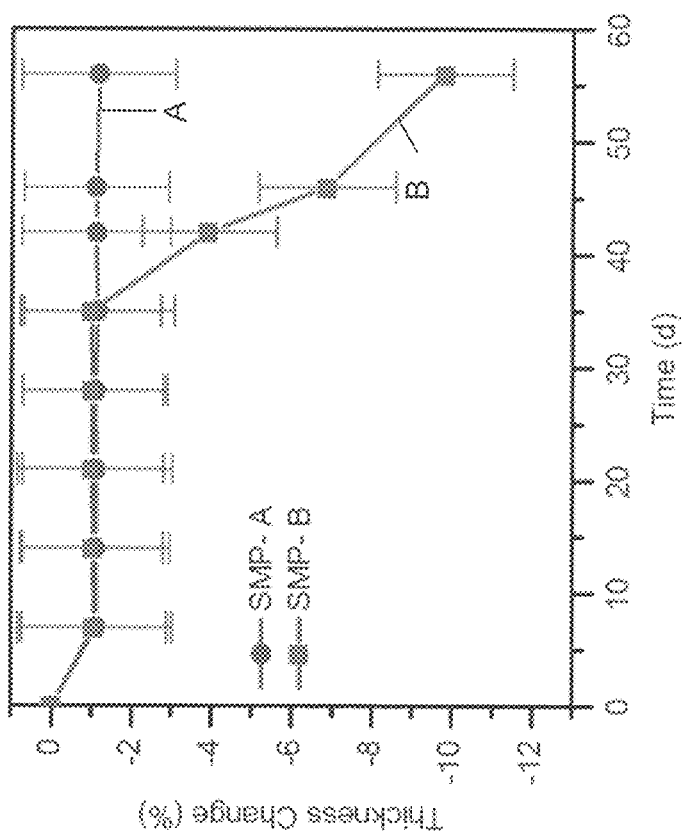
FIG. 2B presents example thickness changes in SMP-A and SMP-B samples after various simulated aging times in PBS at 75° C.
Figure 2A:
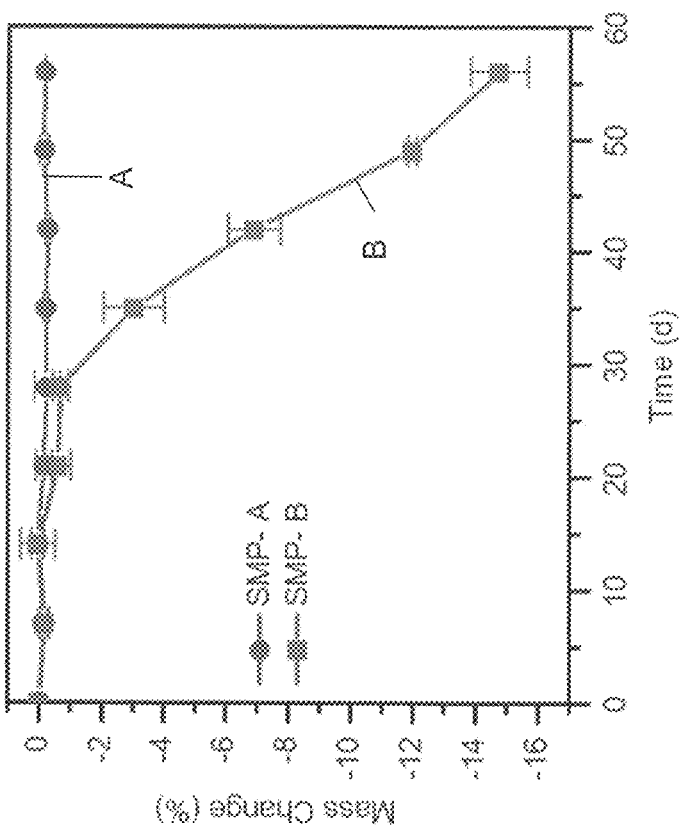
FIG. 2A presents example mass changes in SMP-A and SMP-B samples after various simulated aging times in PBS at 75° C.

In one series of aging tests, to measure and compare the hydrolytic stability of SMP-A and SMP-B samples under simulated physiological conditions, aging in PBS at 75° C. was performed. Changes in the sample's mass and thickness was measured. As shown in FIG. 2A, the mass of SMP-B samples was substantially stable for about four weeks, but thereafter began to continually lose mass until the test was stopped. After eight weeks at elevated temperature SMP-B samples lost 14.7±0.9% (mean±SEM) of their original mass. In comparison, SMP-A samples exhibited substantially no weight loss over the 8 week study period. A similar trend in sample thickness was observed, where SMP-A samples had no substantial change in thickness over the testing period, whereas the thickness of SMP-B samples began to decrease after about five weeks and at the end of eight weeks had lost 9.8±1.6% of their original thickness.

In another series of aging tests, the hydrolytic stability of SMP-A and SMP-B, the mass (FIG. 3A) and thickness (FIG. 3B) of samples were measured and compared in 1.0 M NaOH at 37° C. as compared to the initial pristine and dry polymers (time=0). Over the course of the four week study period, SMP-A samples had substantially no loss of mass, but SMP-B samples had a substantial decrease in mass, with a decrease of 38.74±0.3% after 4 weeks. Similarly, the thickness of SMP-B samples decreased substantially (42.1±1.7% after 4 weeks) while the thickness of SMP-A samples remained substantially stable over the study period.

Cytotoxicity Testing

Figure 4B:
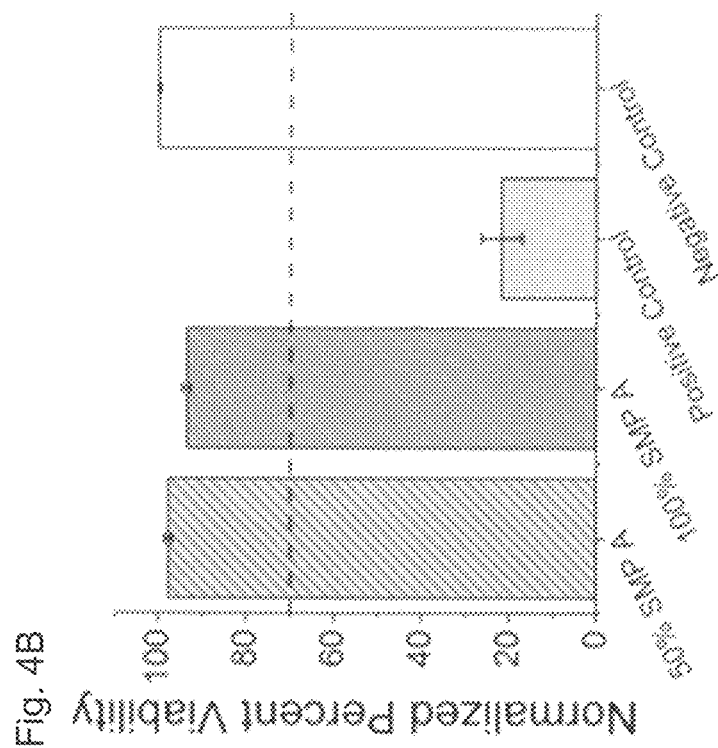
FIG. 4B presents example mean normalized cell viability percentage of SMP-A samples at 50% and 100% concentrations, positive control, and negative control, where the dashed line represents the 70% threshold needed to pass for non-cytotoxic materials.
Figure 4A:
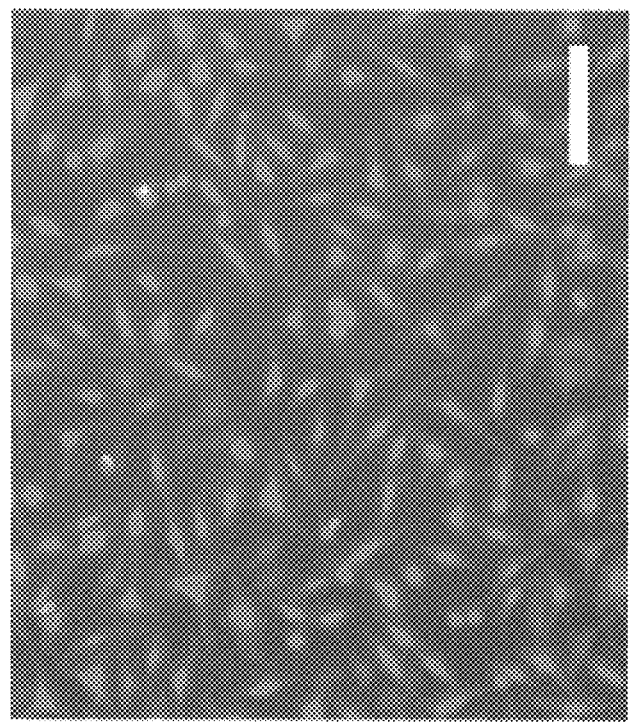
FIG. 4A presents an example fluorescent image of NCTC fibroblasts stained with CaAM (green) and EthD-1 (red) in the presence of SMP-A, where green cells represent live cells and red cells represent apoptotic cells. Scale bar represents 100 μm.

We carried out live/dead assays to assess the cytotoxicity of SMP-A samples in vitro, based on material extract treatments in accordance with ISO protocol 10993-5. After fibroblasts were incubated for 24 hours in the material extract, cell viability percentages were calculated and normalized to the negative control (FIG. 4A). SMP-A samples at 50% and 100% concentrations had normalized viability percentages of 97.8±0.8% (mean±SEM, n=6) and 93.6±1% (mean±SEM, n=6), respectively. The positive control had a significantly lower viability percentage of 21.8±4.7% (mean±SEM, n=6) (FIG. 4B). Normalized viability percentages for SMP-A at both 50% and 100% concentrations were both above the 70% threshold and deemed non-cytotoxic in accordance with ISO protocol 10993-5.

To further illustrate various features of the disclosure, the fabrication of non-limiting example bio-electronic devices, which include embodiments of the thiol-ene SMP of the disclosure, and characteristics of the device, are presented below.

Bio-Electronic Device Fabrication

FIGS. 5A-5L presents selected steps in an example method of manufacturing a bio-electronic device 500 in accordance with the disclosure.

Figure 5B:
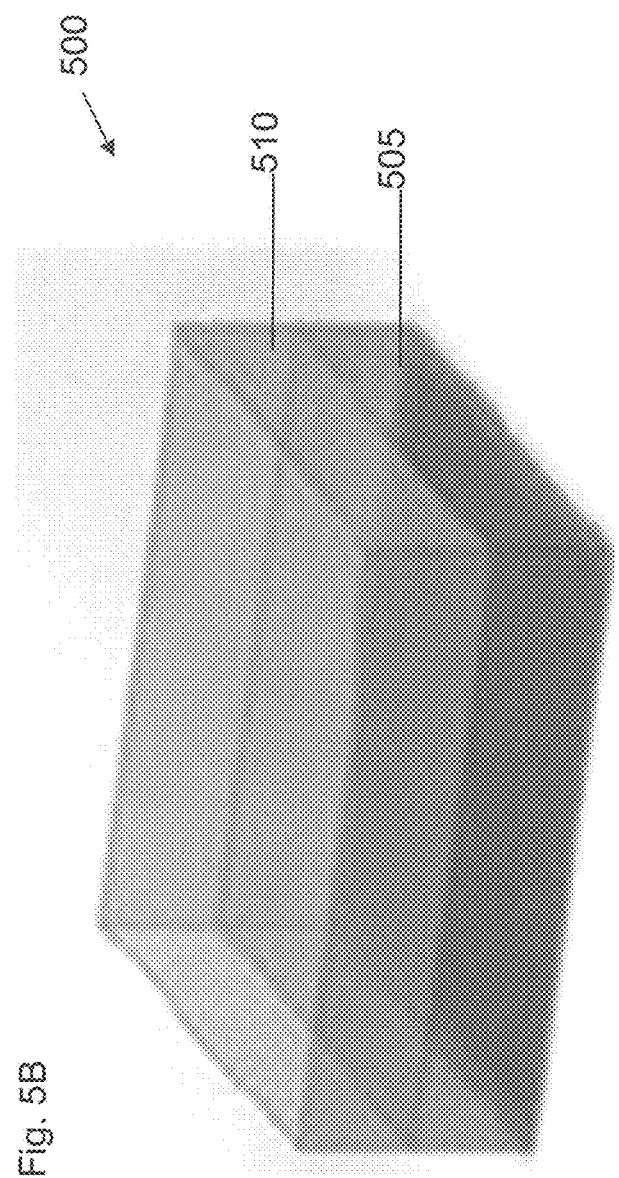

With continuing reference to FIGS. 5A-5I throughout, a base layer 505 (FIG. 5A, e.g., a carrier glass slide, glass substrate or a silicon wafer) is provided and, a reaction mixture layer 510 is deposited on the base layer (FIG. 5B, e.g., an about 50 μm thick layer of the reaction mixture spin-coated on base layer). The reaction mixture can include any of the embodiments of the first types of monomers, second types of monomers and photo-initiate-able catalytic agents disclosed herein, such as TTTSH, DDT, TATATO and DMPA in proportions as described above.

Figure 5C:
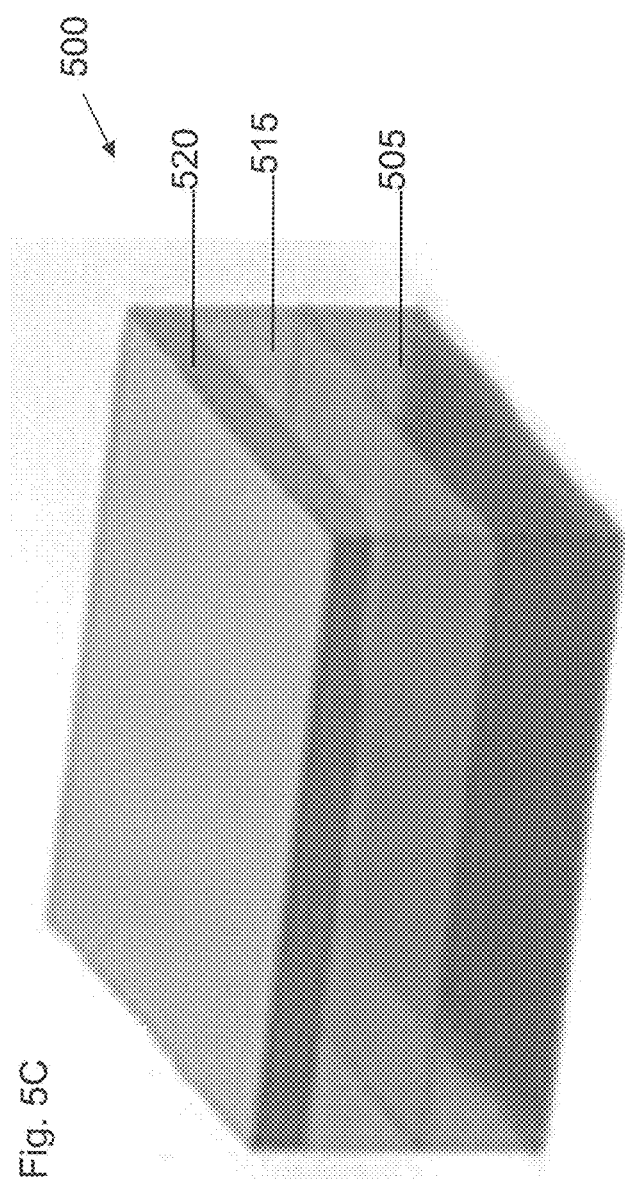

Photo-initiation of the photo-initiate-able catalytic agent (e.g., photo cured under 365 nm UV light) results in formation of a free radical catalyst to thereby initiate step-growth polymerization of the first types of monomers with the second types of monomers to form a sequential chain of the monomers corresponding to a thiol-ene SMP layer 515 (FIG. 5C). Next, a layer of gold 520 was deposited on the polymer layer 515 (FIG. 5C, e.g., an about 300 nm thick Au film is e-beam evaporated on to the polymer layer). A layer of titanium nitride 525 can be deposited on the gold layer 520 (FIG. 5D, e.g., an about 200 nm thick fractal TiN layer deposited using an RF Magnetron Sputtering tool). A protective layer of aluminum 530 can then be deposited on the TiN layer 525 (FIG. 5E, e.g., an about 20 nm thick e-beam evaporated Al layer).

Figure 5G:
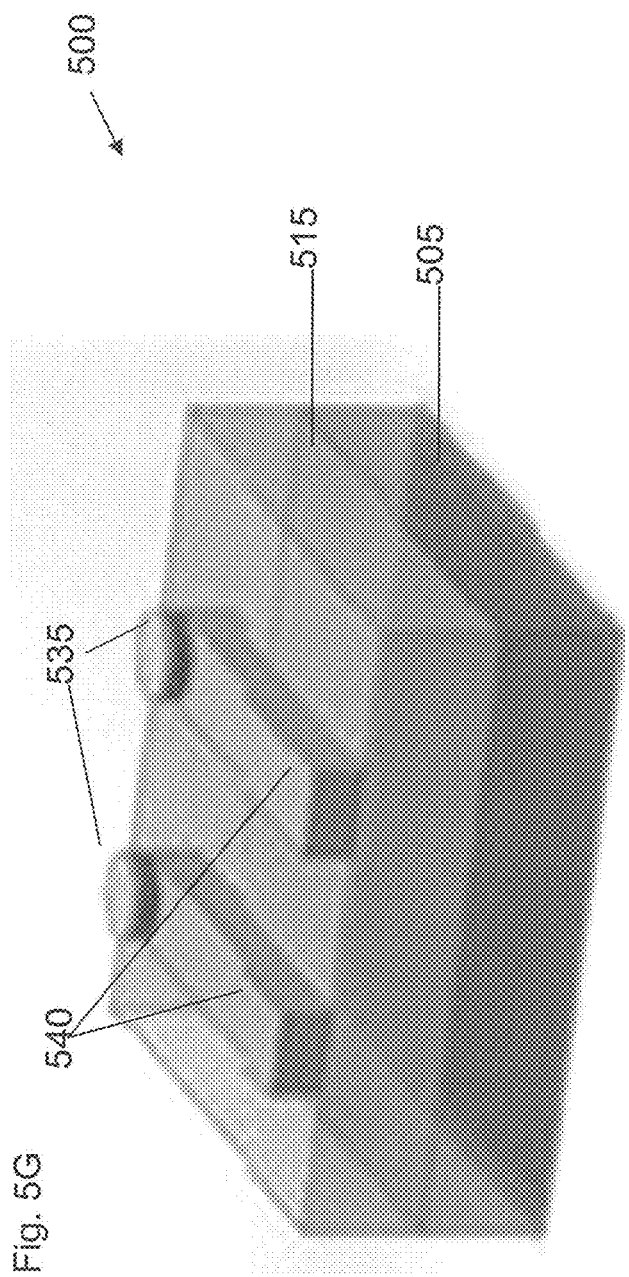
Figure 51:
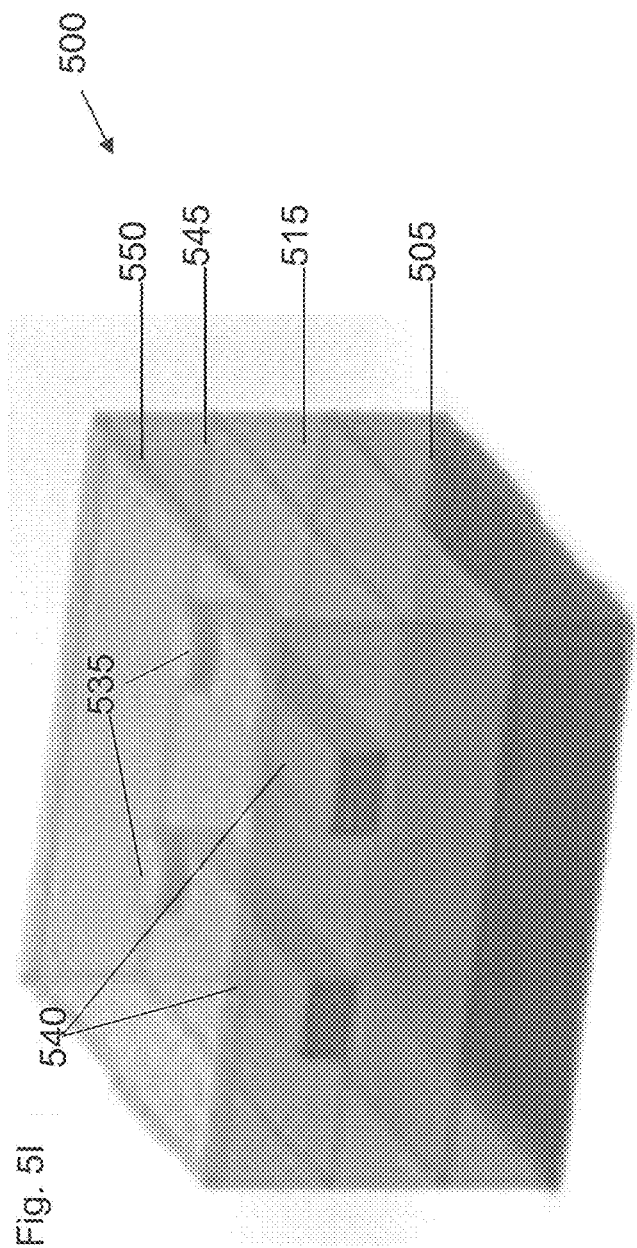
Figure 5J:
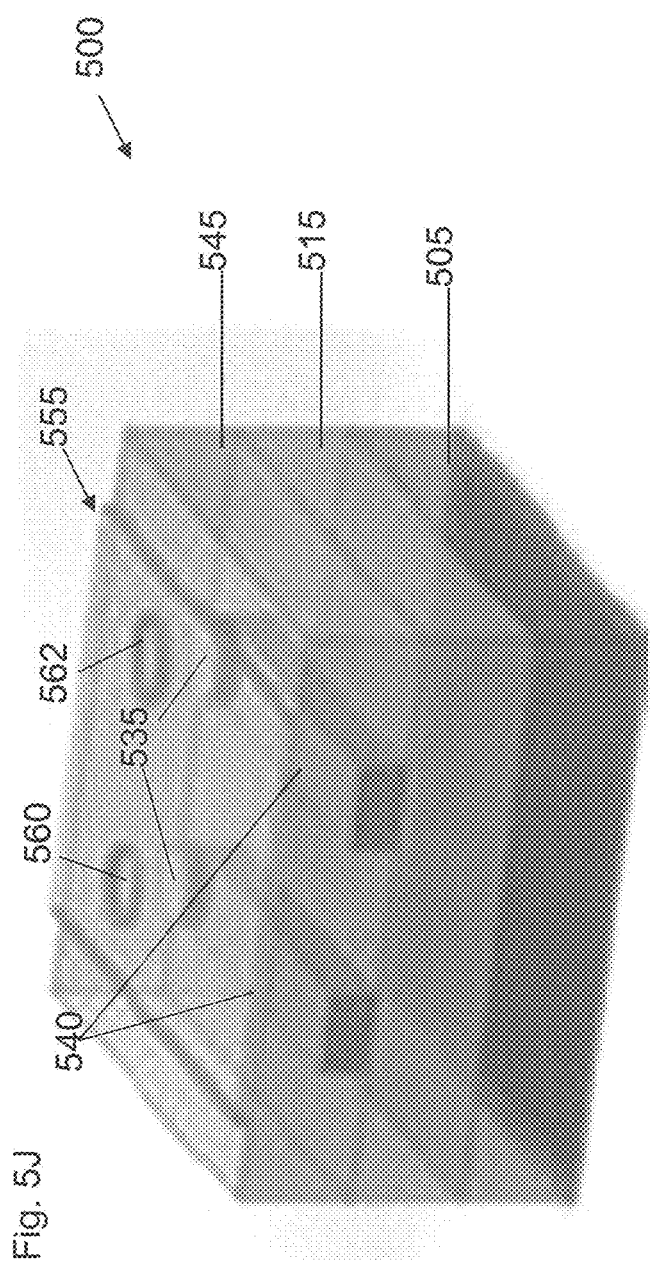

Next, as part of forming an electrode array, photoresist can be deposited on the Al layer 530 (e.g., positive photoresist, S1813, spun onto the Al layer) and then the photoresist patterned using conventional masking and developing procedures. Then device 500 can be immersed in titanium nitride etchant resulting in the formation of TiN electrodes 535 (FIG. 5F, e.g., about 500 μm diameter circularly-shaped electrode). The exposed gold layer 520 (FIG. 5F) can then be treated with a similar photolithography process using a different photoresist and mask set to form patterned Au interconnect layers 540 (FIG. 5G).

Next, another thiol-ene SMP layer 545 can be formed on the device 500 including on the TiN electrodes 535 and Au interconnect layers 540 by depositing another reaction mixture of the first and second monomers and photo-initiateable catalytic agent on the device 500 (e.g., an about 50 μm thick layer spin coated on to the device 500) and then cured by photo-initiating the photo-initiate-able catalytic agent, similar to that described above, to form the second thiol-ene SMP layer 545 (FIG. 5H). A hard mask layer 550 can then be deposited on to the second polymer layer (FIG. 5I), e.g., an about 150 nm thick silicon nitride, SiN, hard mask layer 550.

Another photolithography process can then be done followed by reaction ion dry etch (RIE) to remove exposed portions of the hard mask layer 550 to produce a patterned hard mask layer 555 (FIG. 5J) that covers and protects the electrode and interconnect layer 535, 540. Next, a RIE oxygen plasma process can be performed to remove excess polymer to form openings (FIG. 5K, e.g., openings 560, 562) for the electrode vias, wire connection pads and form an outline of a polymer-enclosed electrode array 565 (FIG. 5K). The removal of the excess polymer not covered by patterned hard mask layer 555 can be followed by a SiN and Al wet etching process to remove the polymer-enclosed electrode array 565 from the base layer 505 and provide the polymer-enclosed electrode array 565 of the device 500 (FIG. 5L).

The fabricated device 500 was then used for subsequent characterization for use with the polymer-enclosed electrode array 565 configured as prototype spinal cord stimulation (SCS) arrays.

Device Characterization

Example devices, configured with SCS arrays, were electrochemically evaluated using cyclic voltammetry (CV) and electrochemical impedance measurements (EIS).

Figure 6B:
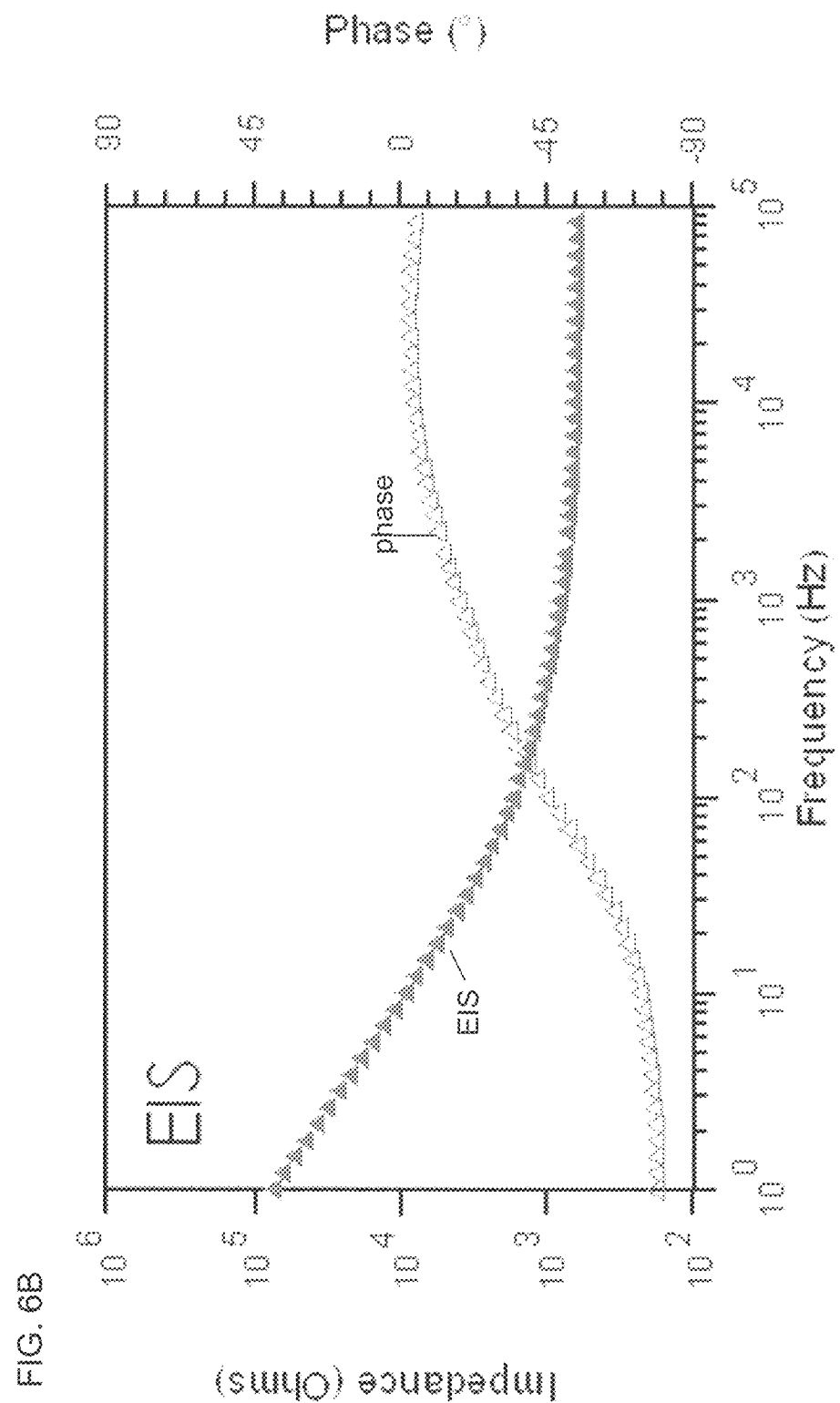
FIG. 6B presents example electrochemical impedance (EIS) and phase measurement results obtained for an example bio-electronic device of disclosure.

As shown in FIG. 6A, the SCS arrays were characterized electrochemically to benchmark performance CV showing a characteristic TiN electrode curve performed at 50 mV scan rate in PBS 1+ using a Ag|AgCl reference electrode and Pt wire as a counter electrode. As shown in FIG. 6B, EIS measured impedance and phase angle as a function of frequency of the TiN electrodes. Impedance of 787 ohms at 1 kHz suggests capacitive behavior at low frequencies as expected.

The measurements show that the devices were fully encapsulated by the thiol-ene based SMPs layers with ester-free backbones (e.g., FIG. 5L, layers 515, 545) and that the TiN electrodes (e.g., electrodes 535) performed similar to analogous devices fabricated with SMP layers with ester-containing backbones.

DISCUSSION

Both SMP-A and SMP-B were synthesized utilizing a thiol-click polymerization mechanism and the glass transitions were tuned to 42-46° C. in dry conditions and around 34° C. when immersed in PBS. The mechanical properties of the SMPs changed in the aqueous environment due to the plasticization effect of water molecules on polymer films. The storage modulus E' decreased significantly after 25 and 10 min immersion in PBS at 37° C., for SMP-A and SMP-B, respectively. Therefore, the glass transition in dry condition is high enough for handling during insertion and low enough to not cause an inflammatory response under physiological conditions. After finding the proper composition for both SMPs, the polymers were evaluated for long-term stability in two different media: phosphate buffer saline to mimic the blood and tissue of human body at elevated temperature (75° C.) and a harsher alkaline solution at 37° C. Afterward, the weight loss and thermomechanical properties of the SMPs were investigated.

The weight loss and thickness loss data of polymers in PBS (FIGS. 2A and 2B) indicate that SMP-B is stable until the fourth week, but after that begins to continually lose weight and thickness up to 15% and 10%, respectively. According to Arrhenius equation, aging test at 75° C. for one week is equivalent to fourteen weeks at body temperature. Therefore, SMP-B starts to degrade after about fifty-six weeks (13 Months). SMP-A data shows that ester-free polymers are stable under these conditions. Harsh conditions were used to further accelerate aging.

Figure 3B:
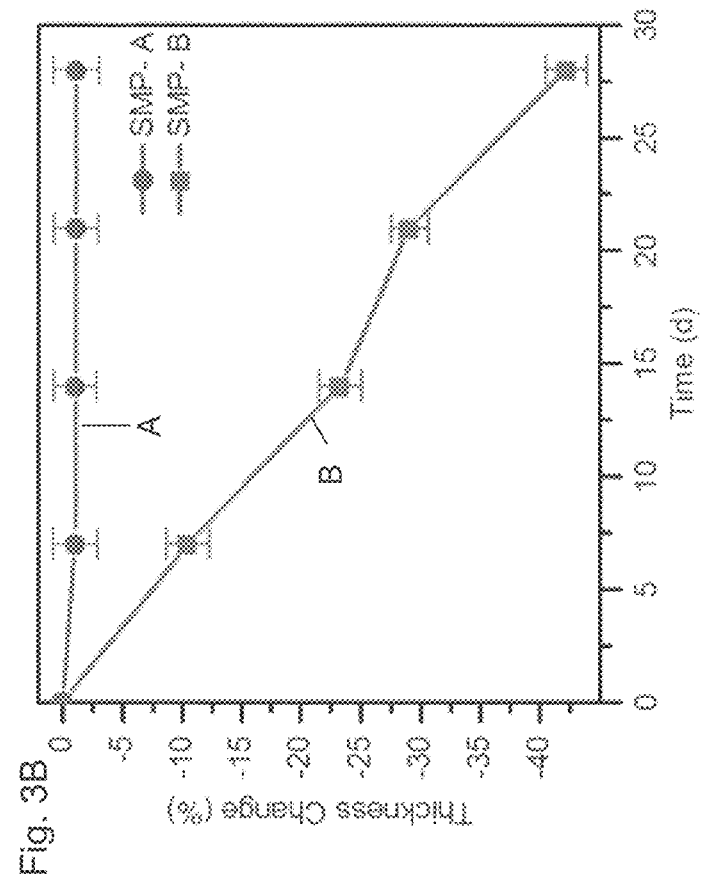
FIG. 3B presents example thickness changes in SMP-A and SMP-B samples after various simulated aging times in 1.0 M NaOH at 37° C.
Figure 3A:
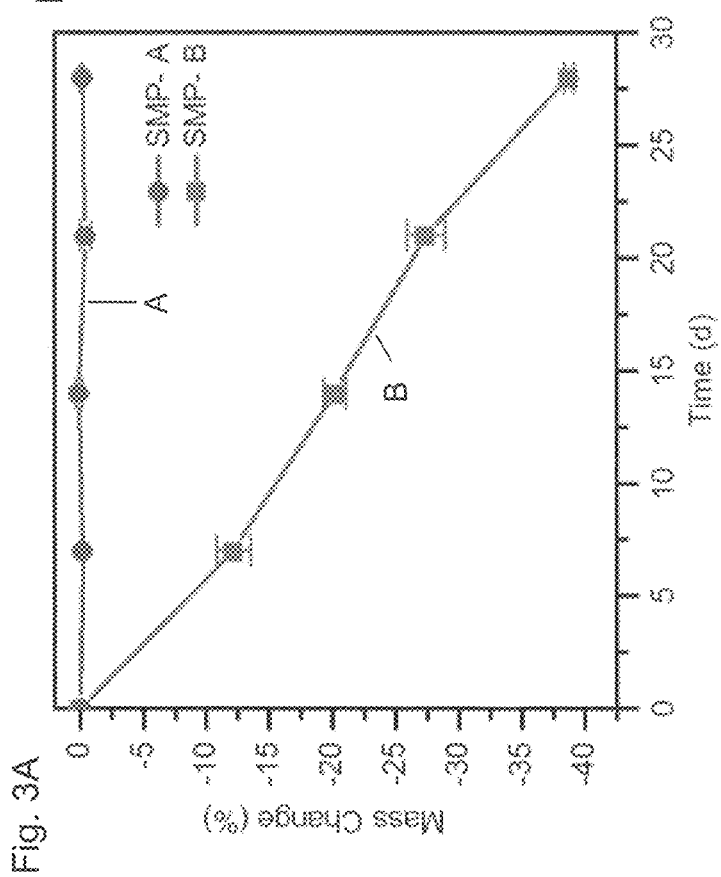
FIG. 3A presents example mass changes in SMP-A and SMP-B samples after various simulated aging times in 1.0 M NaOH at 37° C.

FIGS. 3A and 3B shows the weight loss and thickness loss of SMP-A and SMP-B in NaOH solution. According to the graphs, SMP-A, which does not contain ester groups, is completely stable and the weight and thickness did not change. On the other hand, ester-group containing SMP-B started to hydrolyze which leads to a 38% and 42% decrease in weight and thickness respectively after four weeks. It was seen that maximum weight loss in PBS at 75° C. after eight weeks was 15%, which was the same as for NaOH after nine days. Therefore, in NaOH at 37° C. SMP-B hydrolyzes six times faster than in PBS at 75° C. and the SMP-A is projected to be stable for at least 7 years under real time, physiological conditions.

Those skilled in the art to which this application relates will appreciate that other and further additions, deletions, substitutions and modifications may be made to the described embodiments.

What is claimed is:
1. A bio-electronic device, comprising:
   a substrate layer composed of a thiol-ene shape memory polymer, the polymer including:
      a sequential chain of a first type of monomer covalently bonded to a second type of monomer via thiol-ene linkages that form a backbone of the polymer, wherein:
         the first type of monomer is 1,3,5-tris(3-mercaptopropyl)-1,3,5-triazinane-2,4,6-trione (TTTSH),
         and, the second type of monomer is a mixture of 1,3,5-triallyl-1,3,5-triazine-2,4,6-trione (TATATO) and 2,4,6-tris(2-allyloxy)ethoxy)-1,3,5-triazine (TAET), the sequential chain of the covalently bonded first and second types of monomers forming the polymer backbone is free of ester groups, and at least one patterned gold interconnect line adhered to the substrate layer and a second substrate layer composed of the thiol-ene shape memory polymer, covering the substrate layer and the gold interconnect lines and having an opening therein.

2. A bio-electronic device, comprising:

a substrate layer composed of a thiol-ene shape memory polymer, the polymer including:

a sequential chain of a first type of monomer covalently bonded to a second type of monomer via thiol-ene linkages that form a backbone of the polymer, wherein:

the first type of monomer includes two or more thiol functional groups and the second type of monomer includes two or more alkene functional groups, the sequential chain of the covalently bonded first and second types of monomers forming the polymer backbone is free of ester groups, and at least one patterned gold interconnect line adhered to the substrate layer, an iridium oxide electrode layer on a portion of the at least one gold interconnect line and a second substrate layer composed of the thiol-ene shape memory polymer, covering the substrate layer and the gold interconnect lines and having an opening therein, the iridium oxide electrode layer exposed through the opening.

3. A bio-electronic device, comprising:

a substrate layer composed of a thiol-ene shape memory polymer, the polymer including:

a sequential chain of a first type of monomer covalently bonded to a second type of monomer via thiol-ene linkages that form a backbone of the polymer, wherein:

the first type of monomer includes two or more thiol functional groups and the second type of monomer includes two or more alkene functional groups, the sequential chain of the covalently bonded first and second types of monomers forming the polymer backbone is free of ester groups, and at least one patterned gold interconnect line adhered to the substrate layer, a platinum electrode layer on a portion of the at least one gold interconnect line and a second substrate layer composed of the thiol-ene shape memory polymer, covering the substrate layer and the gold interconnect lines and having an opening therein, the platinum electrode layer exposed through the opening.

* * * * *

UNITED STATES PATENT AND TRADEMARK OFFICE
CERTIFICATE OF CORRECTION

PATENT NO.         : 11,584,867 B2                                            Page 1 of 1
APPLICATION NO.    : 17/569702
DATED              : February 21, 2023
INVENTOR(S)        : Walter Voit, Melanie Ecker and Seyed Mahmoud Hosseini It is certified that error appears in the above-identified patent and that said Letters Patent is hereby corrected as shown below:

In the Specification

In Column 12, Lines 53-65, delete:

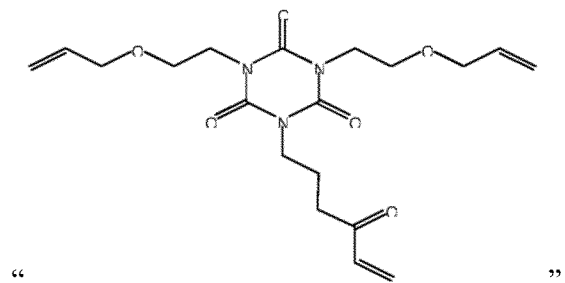

"                                      "

And insert:

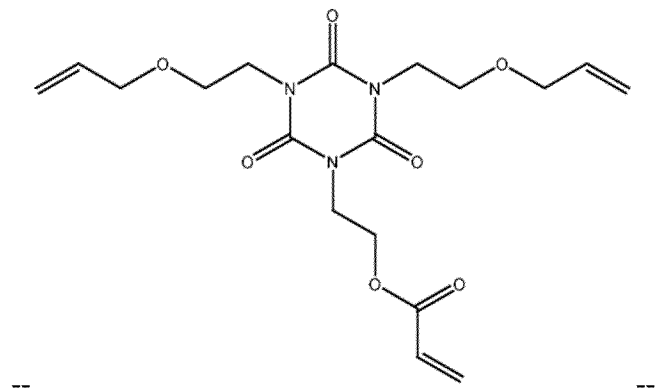

--                                      --

Signed and Sealed this
Twentieth Day of June, 2023

Katherine Kelly Vidal
*Director of the United States Patent and Trademark Office*